United States Patent
Tomat et al.

(10) Patent No.: US 11,504,346 B2
(45) Date of Patent: Nov. 22, 2022

(54) REDOX-ACTIVATED PRO-CHELATORS

(71) Applicant: ARIZONA BOARD OF REGENTS ON BEHALF OF THE UNIVERSITY OF ARIZONA, Tucson, AZ (US)

(72) Inventors: Elisa Tomat, Tucson, AZ (US); Tsuhen Chang, Tucson, AZ (US); Eman A. Akam, Tucson, AZ (US)

(73) Assignee: ARIZONA BOARD OF REGENTS ON BEHALF OF THE UNIVERSITY OF ARIZONA, Tucson, AZ (US)

( * ) Notice: Subject to any disclaimer, the term of this patent is extended or adjusted under 35 U.S.C. 154(b) by 0 days.

Patent file contains an affidavit/declaration under 37 CFR 1.130(b).

(21) Appl. No.: 16/200,286

(22) Filed: Nov. 26, 2018

(65) Prior Publication Data

US 2019/0091183 A1 Mar. 28, 2019

Related U.S. Application Data

(63) Continuation-in-part of application No. 16/014,905, filed on Jun. 21, 2018, now abandoned, which is a continuation-in-part of application No. PCT/US2016/068061, filed on Dec. 21, 2016, application No. 16/200,286, which is a continuation-in-part of application No. 15/345,393, filed on Nov. 7, 2016, now abandoned, which is a continuation of application No. 14/531,634, filed on Nov. 3, 2014, now Pat. No. 9,486,423.

(60) Provisional application No. 62/270,246, filed on Dec. 21, 2015, provisional application No. 61/899,262, filed on Nov. 3, 2013.

(51) Int. Cl.
| | |
|---|---|
| *A61K 31/175* | (2006.01) |
| *C07D 307/64* | (2006.01) |
| *C07D 249/08* | (2006.01) |
| *C07C 337/04* | (2006.01) |
| *C07D 277/36* | (2006.01) |

(52) U.S. Cl.
CPC .......... *A61K 31/175* (2013.01); *C07C 337/04* (2013.01); *C07D 249/08* (2013.01); *C07D 277/36* (2013.01); *C07D 307/64* (2013.01)

(58) Field of Classification Search
None
See application file for complete search history.

(56) References Cited

U.S. PATENT DOCUMENTS

| | | |
|---|---|---|
| 5,246,821 A | 9/1993 | Abe et al. |
| 6,030,846 A | 2/2000 | Simons et al. |
| 7,488,747 B2 | 2/2009 | Fang et al. |
| 7,825,226 B2 | 11/2010 | Schultz et al. |
| 8,551,976 B2 | 10/2013 | Franz et al. |
| 8,680,077 B2 | 3/2014 | Franz et al. |
| 8,685,955 B2 | 4/2014 | Youdim et al. |
| 9,486,423 B2 | 11/2016 | Tomat et al. |
| 2006/0252798 A1 | 11/2006 | Richardson et al. |
| 2012/0276163 A1 | 11/2012 | Tselepis et al. |
| 2013/0310346 A1 | 11/2013 | Zurawski |
| 2014/0073645 A1 | 3/2014 | Linder et al. |
| 2014/0206725 A1 | 7/2014 | Richardson et al. |
| 2015/0126610 A1 | 5/2015 | Tomat et al. |
| 2017/0112788 A1 | 4/2017 | Tomat et al. |

FOREIGN PATENT DOCUMENTS

| | | |
|---|---|---|
| WO | WO2015200916 A2 | 12/2015 |
| WO | WO2017112787 A1 | 6/2017 |

OTHER PUBLICATIONS

What is an Atom? Electronic Resource: [http://www.qrg.northwestern.edu/projects/vss/docs/propulsion/1-what-is-an-atom.html], Retrieved on Jan. 22, 2020.*
Database Registry Chemical Abstracts Service, Columbus, Ohio, Accession No. RN 1440088-84-5. Entered STN: Jun. 21, 2013.*
Kotte, Stephan. Investigations on Structural and Electrochemical Properties of Some Disulfides Prepared by Schiff Base Reactions. J. Prakt. Chem. 2000, 342, No. 1, p. 1-5.*
Database Registry Chemical Abstracts Service, Columbus, Ohio, Accession No. RN 21503-20-8. Entered STN: Nov. 16, 1984.*
Chang Tsuhen M. Disulfide/thiol switches in thiosemicarbazone ligands for redox-directed iron chelaton. Dalton Trans. 2013, 42, 7846-7849.*
Akam, E. A.; Chang, T. M.; Astashkin, A. V.; Tomat, E. "Intracellular reduction/activation of a disulfide switch in thiosemicarbazone iron chelators" Metallomics 2014, 6, 1905-1912.
Chang, T. M.; Tomat, E. "Disulfide/thiol switches in thiosemicarbazone ligands for redox-directed iron chelation" Dalton Trans. 2013, 42, 7846-7849.
Vazquez-Dorbatt et al., Synthesis of a Pyridyl Disulfide End-Functionalized Glycopolymer for Conjugation to Biomolecules and Patterning on Gold Surfaces, NIH Public Access, Author Manuscript, Aug. 10, 2010, entire document.
Cal Varesi et al., Glucose conjugation for the specific targeting and treatment of cancer, Chemical Science, vol. 4, 2013, pp. 2319-2333.
Samukov, A Simple Preparation of 3-(2-Pyridyldithio)-Propionic Acid, Synthetic Communications, vol. 28, No. 17, 1998. pp. 3213-3217.
Akam et al., Targeting Iron in Colon Cancer via Glycoconjugation of Thiosemicarbazone Prochelators. Bioconjugate Chemistry. vol. 27.Jul. 29, 2016. pp. 1807-1812.

(Continued)

*Primary Examiner* — Samantha L Shterengarts
(74) *Attorney, Agent, or Firm* — Nguyen Tarbet LLC

(57) ABSTRACT

Compositions of pro-chelator compounds are described herein. The pro-chelators may be activated in reducing conditions, such as in the intracellular space, so as to sequester metals such as iron. The pro-chelators may be used to target malignant cells or in the treatment in a condition associated with metal ion disregulation.

13 Claims, 4 Drawing Sheets

(56) References Cited

OTHER PUBLICATIONS

Ferlay, J., Soerjomataram, I., Dikshit, R., Eser, S., Mathers, C., Rebelo, M., Parkin, D. M., Forman D., and Bray, F. (2015) Cancer incidence and mortality worldwide: sources, methods and major patterns in GLOBOCAN 2012. Int. J. Cancer 136, E359-386.

Bingham, S., and Riboli, E. (2004) Diet and cancer—the European Prospective Investigation into Cancer and Nutrition. Nat Rev. Cancer 4, 206-215.

Nelson, R. L. (2001) Iron and colorectal cancer risk: Human studies. Nutr. Rev. 59, 140-148.

Chua, A. C., Klopcic, B., Lawrance, I. C., Olynyk, J. K., and Trinder, D. (2010) Iron: an emerging factor in colorectal carcinogenesis. World J. Gastroenterol. 16, 663-672.

Padmanabhan, H., Brookes, M. J., and Iqbal, T. (2015) Iron and colorectal cancer: evidence from in vitro and animal studies. Nutr. Rev. 73, 308-317.

Brookes, M. J., Hughes, S., Turner, F. E., Reynolds, G., Sharma, N., Ismail, T., Berx, G., McKie, A. T., Hotchin, N., Anderson, G. J., et al. (2006) Modulation of iron transport proteins in human colorectal carcinogenesis. Gut 55, 1449-1460.

Torti, S. V., and Torti, F. M. (2013) Iron and cancer: more ore to be mined. Nat. Rev. Cancer 13, 342-355.

Merlot, A. M., Kalinowski, D. S., and Richardson, D. R. (2013) Novel Chelators for Cancer Treatment: Where Are We Now? Antioxid. Redox. Sign. 18, 973-1006.

Kalinowski, D. S., and Richardson, D. R. (2005) The evolution of iron chelators for the treatment of iron overload disease and cancer. Pharmacol. Rev. 57, 547-583.

Perez, L. R., and Franz, K. J. (2010) Minding metals: tailoring multifunctional chelating agents for neurodegenerative disease. Dalton Trans. 39, 2177-2187.

Lee, M. H., Yang, Z., Lim, C. W., Lee, Y. H., Dongbang, S., Kang, C., and Kim, J. S. (2013) Disulfide-Cleavage-Triggered Chemosensors and Their Biological Applications. Chem. Rev. 113, 5071-5109.

Lee, M. H., Sessler, J. L., and Kim, J. S. (2015) Disulfide-Based Multifunctional Conjugates for Targeted Theranostic Drug Delivery. Acc. Chem. Res. 48, 2935-2946.

Yu, Y., Kalinowski, D. S., Kovacevic, Z., Siafakas, A. R., Jansson, P. J., Stefani, C., Lovejoy, D. B., Sharpe, P. C., Bernhardt, P. V., and Richardson, D. R. (2009) Thiosemicarbazones from the old to new: iron chelators that are more than just ribonucleotide reductase inhibitors. J. Med. Chem. 52, 5271-5294.

Vander Heiden, M. G. (2011) Targeting cancer metabolism: a therapeutic window opens. Nat. Rev. Drug Discov. 10, 671-684.

Calvaresi, E. C., and Hergenrother, P. J. (2013) Glucose conjugation for the specific targeting and treatment of cancer. Chem. Sci. 4, 2319-2333.

Younes, M., Lechago, L. V., and Lechago, J. (1996) Overexpression of the human erythrocyte glucose Yansporter occurs as a late event in human colorectal carcinogenesis and is associated with an increased incidence of lymph node metastases. Clin. Cancer Res. 2, 1151-1154.

Haber, R. S., Rathan, A., Weiser, K. R., Pritsker, A., Itzkowitz, S. H., Bodian, C., Slater, G., Weiss, A., and Burstein, D. E. (1998) GLUT1 glucose transporter expression in colorectal carcinoma—A marker for poor prognosis. Cancer 83, 34-40.

Shen, Y. M., Arbman, G., Olsson, B., and Sun, X. F. (2011) Overexpression of GLUT1 in colorectal cancer is independently associated with poor prognosis. Int. J. Biol. Markers 26, 166-172.

Graziano, F., Ruzzo, A., Giacomini, E., Ricciardi, T., Aprile, G., Loupakis, F., Lorenzini, P., Ongaro, E., Zoratto, F., Catalano, V., et al. (2016) Glycolysis gene expression analysis and selective metabolic advantage in the clinical progression of colorectal cancer. Pharmacogenomics J. DOI: 10.1038/tpj.2016.13.

Mikata, Y., and Gottschaldt, M. (2014) Metal Complexes of Carbohydrate-targeted Ligands in Medicinal Inorganic Chemistry. Ligand Design in Medicinal Inorganic Chemistry (Storr, T., Ed.) pp. 145-173, Chapter 6, John Wiley & Sons, Ltd, Chichester, UK.

Ju, P. X., Lu, Y. H., Gao, X. Q., Liu, R., Zhang-Negrerie, D., Shi, Y., Wang, Y. Q., Wang, S. Q., and Gao, Q. Z. (2013) Highly water-soluble platinum(II) complexes as GLUT substrates for targeted therapy: improved anticancer efficacy and transporter-mediated cytotoxic properties. Chem. Commun. 49, 2421-2423.

Patra, M., Johnstone, T. C., Suntharalingam, K., and Lippard, S. J. (2016) A Potent Glucose-Platinum Conjugate Exploits Glucose Transporters and Preferentially Accumulates in Cancer Cells. Angew. Chem. Int. Ed. 55, 2550-2554.

Storr, T., Scott, L. E., Bowen, M. L., Green, D. E., Thompson, K. H., Schugar, H. J., and Orvig, C. (2009) Glycosylated tetrahydrosalens as multifunctional molecules for Alzheimer's therapy. Dalton Trans., 3034-3043.

Pujol, A. M., Cuillel, M., Jullien, A. S., Lebrun, C., Cassio, D., Mintz, E., Gateau, C., and Delangle, P. (2012) A Sulfur Tripod Glycoconjugate that Releases a High-Affinity Copper Chelator in Hepatocytes. Angew. Chem. Int. Ed. 51, 7445-7448.

Cao, J., Cui, S. S., Li, S. W., Du, C. L., Tian, J. M., Wan, S. N., Qian, Z. Y., Gu, Y. Q., Chen, W. R., and Wang, G. J. (2013) Targeted Cancer Therapy with a 2-Deoxyglucose-Based Adriamycin Complex. Cancer Res. 73, 1362-1373.

Halmos, T., Santarromana, M., Antonakis, K., and Scherman, D. (1996) Synthesis of glucose-chlorambucil derivatives and their recognition by the human GLUT1 glucose transporter. Eur. J. Pharmacol. 318, 477-484.

Guenin, R., and Schneider, C. H. (1983) Synthesis and Anaphylactogenicity of Monohaptenic Carbohydrate Conjugates. Helv. Chim. Acta 66, 1101-1109.

Fan, W., Wu, Y., Li, X. K., Yao, N., Li, X., Yu, Y. G., and Hai, L. (2011) Design, synthesis and biological evaluation of brain-specific glucosyl thiamine disulfide prodrugs of naproxen. Eur. J. Med. Chem. 46, 3651-3661.

Cui, Y. L., Cheng, Z. D., Mao, J. W., and Yu, Y. P. (2013) Regioselective 6-detrimethylsilylation of per-O-TMS-protected carbohydrates in the presence of ammonium acetate. Tetrahedron Lett. 54, 3831-3833.

Jacob, J. N., and Tazawa, M. J. (2012) Glucose-aspirin: Synthesis and in vitro anti-cancer activity studies. Bioorg. Med. Chem. Lett. 22, 3168-3171.

Peltier-Pain, P., Timmons, S. C., Grandemange, A., Benoit, E., and Thorson, J. S. (2011) Warfarin Glycosylation Invokes a Switch from Anticoagulant to Anticancer Activity. ChemMedChem 6, 1347-1350.

Saaf, A. M., Halbleib, J. M., Chen, X., Yuen, S. T., Leung, S. Y., Nelson, W. J., and Brown, P. O. (2007) Parallels between global transcriptional programs of polarizing caco-2 intestinal epithelial cells in vitro and gene expression programs in normal colon and colon cancer. Mol. Biol. Cell 18, 4245-4260.

Harris, D. S., Slot, J. W., Geuze, H. J., and James, D. E. (1992) Polarized Distribution of Glucose Transporter Isoforms in Caco-2 Cells. Proc. Natl. Acad. Sci. U.S.A. 89, 7556-7560.

O'Neil, R. G., Wu, L., and Mullani, N. (2005) Uptake of a fluorescent deoxyglucose analog (2-NBDG) in tumor cells. Mol. Imaging Biol. 7, 388-392.

Xintaropoulou, C., Ward, C., Wise, A., Marston, H., Turnbull, A., and Langdon, S. P. (2015) A comparative analysis of inhibitors of the glycolysis pathway in breast and ovarian cancer cell line models. Oncotarget 6, 25677-25695.

Barnett, J. E. G., Holman, G. D., and Munday, K. A. (1973) Structural Requirements for Binding to Sugar-Transport System of Human Erythrocyte. Biochem. J. 131, 211-221.

Lin, Y. S., Tungpradit, R., Sinchaikul, S., An, F. M., Liu, D. Z., Phutrakul, S., and Chen, S. T. (2008) Targeting the Delivery of Glycan-Based Paclitaxel Prodrugs to Cancer Cells via Glucose Transporters. J. Med. Chem. 51, 7428-7441.

Sun, X. S., Ge, R. G., Cai, Z. W., Sun, H. Z., and He, Q. Y. (2009) Iron depletion decreases proliferation and induces apoptosis in a human colonic adenocardnoma cell line, Caco2. J. Inorg. Biochem. 103, 1074-1081.

Lane, D. J. R., Mills, T. M., Shafie, N. H., Merlot, A. M., Moussa, R. S., Kalinowski, D. S., Kovacevic, Z., and Richardson, D. R.

(56) References Cited

OTHER PUBLICATIONS (2014) Expanding horizons in iron chelation and the treatment of cancer: Role of iron in the regulation of ER stress and the epithelial-mesenchymal transition. BBA Rev. Cancer 1845, 166-181.
Whitnall, M., Howard, J., Ponka, P., and Richardson, D. R. (2006) A class of iron chelators with a wide spectrum of potent antitumor activity that overcomes resistance to chemotherapeutics. Proc. Natl. Acad. Sci. U.S.A. 103, 14901-14906.
Jansson, P. J., Kalinowski, D. S., Lane, D. J. R., Kovacevic, Z., Seebacher, N. A., Fouani, L., Sahni, S., Merlot, A. M., and Richardson, D. R. (2015) The renaissance of polypharmacology in the development of anti-cancer therapeutics: Inhibition of the "Triad of Death" in cancer by Di-2-pyridylketone thiosemicarbazones. Pharmacol. Res. 100, 255-260.
Medina, R. A., and Owen, G. I. (2002) Glucose transporters: expression, regulation and cancer. Biol. Res. 35, 9-26.
Jung, M. E., Dong, T. A., and Cai, X. L. (2011) Improved synthesis of 4-amino-7-nitrobenz-2,1,3-oxadiazoles using NBD fluoride (NBD-F). Tetrahedron Lett. 52, 2533-2535.
Widdison, W. C., Wilhelm, S. D., Cavanagh, E. E., Whiteman, K. R., Leece, B. A., Kovtun, Y., Goldmacher, V. S., Xie, H. S., Steeves; R. M., Lutz, R. J., et al. (2006) Semisynthetic maytansine analogues for the targeted treatment of cancer. J. Med. Chem. 49, 4392-4408.
Serra, S., Moineaux, L., Vancraeynest, C., Masereel, B., Wouters, J., Pochet, L., and Frederick, R. (2014) Thiosemicarbazide, a fragment with promising indolamine-2,3-dioxygenase (IDO) inhibition properties. Eur. J.Med. Chem. 82, 96-105.
Le, N. T.; Richardson, D. R., The role of iron in cell cycle progression and the proliferation of neoplastic cells. Biochim. Biophys. Acta 2002, 1603, 31-46.
Kwok, J. C.; Richardson, D. R., The iron metabolism of neoplastic cells: Alterations that facilitate proliferation? Crit. Rev. Oncol. Hematol. 2002, 42, 65-78.
Yu, Y.; Wong, J.; Lovejoy, D. B.; Kalinowski, D. S.; Richardson, D. R., Chelators at the cancer coalface: Desferrioxamine to triapine and beyond. Clin. Cancer Res. 2006, 12, 6876-6883.
Richardson, D. R.; Kalinowski, D. S.; Lau, S.; Jansson, P. J.; Lovejoy, D. B., Cancer cell metabolism and the development of potent iron chelators as anti-tumor agents. Biochim. Biophys. Acta 2009, 1790, 720-717.
Sutherland, R.; Delia, O.; Schneider, C.; Newman, R.; Kemshead, J.; Greaves, M., Ubiquitous cell-surface glycoprotein on tumor cells is proliferation-associated receptor for transferrin. Proc. Natl. Acad. Sci. U. S. A. 1981, 78, 4515-4519.
Kontoghiorghes, G. J.; Efstathiou, A.; Ioannou-Loucaides, S.; Kolnagou, A., Chelators controlling metal metabolism and toxicity pathways: Applications in cancer prevention, diagnosis and treatment. Hemoglobin 2008, 32, 217-227.
Dayani, P. N.; Bishop, M. C.; Black, K.; Zeltzer, P. M., Desferoxamine (DFO)-mediated iron chelation: Rationale for a novel approach to therapy for brain cancer. J. Neuro-Oncol. 2004, 67, 367-377.
Nutting, C. M.; Van Herpen, C. M. L.; Miah, A. B.; Bhide, S. A.; Machiels, J. P.; Buter, J.; Kelly, C.; De Raucourt, D.; Harrington, K. J., Phase II study of 3-AP Triapine in patients with recurrent or metastatic head and neck squamous cell carcinoma. Ann. Oncol. 2009, 20, 1275-1279.
Kontoghiorghes, G. J., Ethical issues and risk/benefit assessment of iron chelation therapy: Advances with Deferiprone/Deferoxamine combinations and concerns about the safety, efficacy and costs of Deferasirox. Hemoglobin 2008, 32, 1-15.
Gamcsik, M. P.; Kasibhatla, M. S.; Teeter, S. D.; Colvin, O. M., Glutathione levels in human tumors. Biomarkers 2012, 17, 671-691.
Lee, M. H.; Kim, J. Y.; Han, J. H.; Bhuniya, S.; Sessler, J. L.; Kang, C.; Kim, J. S., Direct Fluorescence Monitoring of the Delivery and Cellular Uptake of a Cancer-Targeted RGD Peptide-Appended Naphthalimide Theragnostic Prodrug. J. Am. Chem. Soc. 2012, 134, 12668-12674.
Wu, X.; Sun, X.; Guo, Z.; Tang, J.; Shen, Y.; James, T. D.; Tian, H.; Zhu, W., In Vivo and in Situ Tracking Cancer Chemotherapy by Highly Photostable NIR Fluorescent Theranostic Prodrug. J. Am. Chem. Soc. 2014, 136, 3579-3588.
Spasojevic, I.; Armstrong, S. K.; Brickman, T. J.; Crumbliss, A. L., Electrochemical Behavior of the Fe(III) Complexes of the Cyclic Hydroxamate Siderophores Alcaligin and Desferrioxamine E. Inorg. Chem. 1999, 38, 449-454.
Bernhardt, P. V., Coordination chemistry and biology of chelators for the treatment of iron overload disorders. Dalton Trans. 2007, 3214-3220.
Ornstein, D. L.; Zacharski, L. R., Iron stimulates urokinase plasminogen activator expression and activates NF-kappa B in human prostate cancer cells. Nutr. Cancer 2007, 58, 115-126.
Kalinowski, D. S.; Yu, Y.; Sharpe, P. C.; Islam, M.; Liao, Y. T.; Lovejoy, D. B.; Kumar, N.; Bernhardt, P. V.; Richardson, D. R., Design, synthesis, and characterization of novel iron chelators: Structure-activity relationships of the 2-benzoylpyridine thiosemicarbazone series and their 3-nitrobenzoyl analogues as potent antitumor agents. J. Med. Chem. 2007, 50, 3716-3729.
Richardson, D. R.; Kalinowski, D. S.; Richardson, V.; Sharpe, P. C.; Lovejoy, D. B.; Islam, M.; Bernhardt, P. V., 2-Acetylpyridine Thiosemicarbazones are Potent Iron Chelators and Antiproliferative Agents: Redox Activity, Iron Complexation and Characterization of their Antitumor Activity. J. Med. Chem. 2009, 52, 1459-1470.
Choi, J.-Y.; Neuhouser, M. L.; Barnett, M. J.; Hong, C.-C.; Kristal, A. R.; Thornquist, M. D.; King, I. B.; Goodman, G. E.; Ambrosone, C. B., Iron intake, oxidative stress-related genes (MnSOD and MPO) and prostate cancer risk in CARET cohort. Carcinogenesis 2008, 29, 964-970.
Ben-Haim, S.; Ell, P., (18)F-FDG PET and PET/CT in the Evaluation of Cancer Treatment Response. J. Nucl. Med. 2009, 50, 88-99.
Liu, D.-Z.; Sinchaikul, S.; Vasu, P.; Reddy, G.; Chang, M.-Y.; Chen, S.-T., Synthesis of 2 '-paclitaxel methyl 2-glucopyranosyl succinate for specific targeted delivery to cancer cells. Bioorg. Med. Chem. Lett. 2007, 17, 617-620.
Bensinger, S. J.; Christofk, H. R., New aspects of the Warburg effect in cancer cell biology. Semin. Cell Dev. Biol. 2012, 23, 352-361.
Yoshioka, K.; Takahashi, H.; Homma, T.; Saito, M.; Oh, K. B.; Nemoto, Y.; Matsuoka, H., A novel fluorescent derivative of glucose applicable to the assessment of glucose uptake activity of *Escherichia coli*. Biochim. Biophys. Acta 1996, 1289, 5-9.
Heath, J.L. et al., Iron Deprivation in Cancer—Potential Therapeutic Implications. Nutrients. Aug 2013; 5(8): 2836-2859.
Kovacevic, Z. et al., Iron Chelators: Development of Novel Compounds with High and Selective Anti-Tumour Activity. Current Drug Delivery, vol. 7, No. 3, Jul. 2010, pp. 194-207(14).
Buss, JL, et al., Iron chelators in cancer chemotherapy. Curr Top Med Chem. 2004;4(15):1623-35.
Chitambar, CR, et al. Iron-targeting antitumor activity of gallium compounds and novel insights into triapine(®)-metal complexes. Antioxid Redox Signal. Mar. 10, 2013;18(8):956-72.
Yu, Y., et al. The Potent and Novel Thiosemicarbazone Chelators Di-2-pyridylketone-4, 4-dimethyl-3-thiosemicarbazone and 2-Benzoylpyridine-4, 4-dimethyl-3-thiosemicarbazone Affect Crucial Thiol Systems Required for Ribonucleotide Reductase Activity. Molecular Pharmacology Jun. 2011 vol. 79 No. 6 921-931.
Gamini Siriwardana and Paul A. Seligman. Two cell cycle blocks caused by iron chelation of neuroblastoma cells: separating cell cycle events associated with each block. Physiol Rep. Dec 1, 2013; 1(7): e00176.
Choi, J.G., et al. Effects of oral iron chelator deferasirox on human malignant lymphoma cells. Korean J Hematol. Sep 2012; 47(3): 194-201.
Loccufier, J.; Schacht, E., Convenient Method for the Preparation of 3-(2-Pyridyl Dithio) Propionic-Acid N-Hydroxy Succinimide Ester. B Soc Chim Belg. 1988, 97, 535-539.
Wood, T. E.; Thompson, A., Chem. Rev. 2007, 107, 1831-1861.
Gryko, D. T.; Gryko, D.; Lee, C.-H., Chem. Soc. Rev. 2012, 41, 3780-3789.
Katayev, E. A.; Severin, K.; Scopelliti, R.; Ustynyuk, Y. A., Inorg. Chem. 2007, 46, 5465-5467.
Reid, S. D.; Wilson, C.; Blake, A. J.; Love, J. B., Dalton Trans. 2010, 39, 418-425.
Halper, S. R.; Cohen, S. M., Inorg. Chem. 2005, 44, 486-488.

(56) References Cited

OTHER PUBLICATIONS

King, E. R.; Betley, T. A., Inorg. Chem. 2009, 48, 2361-2363.
King, E. R.; Sazama, G. T.; Betley, T. A., J. Am. Chem. Soc. 2012, 134, 17858-17861.
Hennessy, E. T.; Betley, T. A., Science 2013, 340, 591-595.
Thoi, V. S.; Stork, J. R.; Niles, E. T.; Depperman, E. C.; Tierney, D. L.; Cohen, S. M., Inorg. Chem. 2008, 47, 10533-10541.
Patra, A. K.; Dube, K. S.; Sanders, B. C.; Papaefthymiou, G. C.; Conradie, J.; Ghosh, A.; Harrop, T. C., Chem. Sci. 2012, 3, 364-369.
Sanders, B. C.; Patra, A. K.; Harrop, T. C., J. Inorg. Biochem. 2013, 118, 115-127.
Broering, M.; Koehler, S.; Pietzonka, C., J. Porph. Phthalocy. 2012, 16, 641-650.
Broering, M.; Koehler, S.; Ostapowicz, T.; Funk, M.; Pietzonka, C., Eur. J. Inorg. Chem. 2009, 3628-3635.
Sessler, J. L.; Gebauer, A.; Král, V.; Lynch, V., Inorg. Chem. 1996, 35, 6636-6637.
Bennett, J. W.; Bentley, R., Adv. Appl. Microbiol. 2000, 47, 1-32.
Furstner, A., Angew. Chem., Int. Ed. 2003, 42, 3582-3603.
D'Alessio, R.; Bargiotti, A.; Carlini, O.; Colotta, F.; Ferrari, M.; Gnocchi, P.; Isetta, A.; Mongelli, N.; Motta, P.; Rossi, A.; Rossi, M.; Tibolla, M.; Vanotti, E., J. Med. Chem. 2000, 43, 2557-2565.
Furstner, A.; Grabowski, J.; Lehmann, C. W.; Kataoka, T.; Nagai, K., ChemBioChem 2001, 2, 60-68.
Marchal, E.; Uddin, M. I.; Smithen, D. A.; Hawco, C. L. A.; Lanteigne, M.; Overy, D. P.; Kerr, R. G.; Thompson, A., RSC Adv. 2013, 3, 22967-22971.
Papireddy, K.; Smilkstein, M.; Kelly, J. X.; Shweta; Salem, S. M.; Alhamadsheh, M.; Haynes, S. W.; Challis, G. L.; Reynolds, K. A., J. Med. Chem. 2011, 54, 5296-5306.
Perez-Tomas, R.; Vinas, M., Curr. Med. Chem. 2010, 17, 2222-2231.
Regourd, J.; Ali, A. A.-S.; Thompson, A., J. Med. Chem. 2007, 50, 1528-1536.
Diaz, R. I. S.; Bennett, S. M.; Thompson, A., ChemMedChem 2009, 4, 742-745.
Smithen, D. A.; Forrester, A. M.; Corkery, D. P.; Dellaire, G.; Colpitis, J.; McFarland, S. A.; Berman, J. N.; Thompson, A., Org. Biomol. Chem. 2013, 11, 62-68.
Melvin, M. S.; Ferguson, D. C.; Lindquist, N.; Manderville, R. A., J. Org. Chem. 1999, 64, 6861-6869.
Sessler, J. L.; Eller, L. R.; Cho, W.-S.; Nicolaou, S.; Aguilar, A.; Lee, J. T.; Lynch, V. M.; Magda, D. J., Angew. Chem., Int. Ed. 2005, 44, 5989-5992.
Davis, J. T.; Gale, P. A.; Okunola, O. A.; Prados, P.; Iglesias-Sanchez, J. C.; Torroba, T.; Quesada, R., Nat. Chem. 2009, 1, 138-144.
Busschaert, N.; Gale, P. A., Angew. Chem., Int. Ed. 2013, 52, 1374-1382.
Melvin, M. S.; Tomlinson, J. T.; Saluta, G. R.; Kucera, G. L.; Lindquist, N.; Manderville, R. A., J. Am. Chem. Soc. 2000, 122, 6333-6334.
Melvin, M. S.; Wooton, K. E.; Rich, C. C.; Saluta, G. R.; Kucera, G. L.; Lindquist, N.; Manderville, R. A., J. Inorg. Biochem. 2001, 87, 129-135.
Diaz, R. I. S.; Regourd, J.; Santacroce, P. V.; Davis, J. T.; Jakeman, D. L.; Thompson, A., Chem. Commun. 2007, 2701-2703.
Furstner, A.; Grabowski, J. E., ChemBioChem 2001, 2, 706-709.
Melvin, M. S.; Tomlinson, J. T.; Park, G.; Day, C. S.; Saluta, G. R.; Kucera, G. L.; Manderville, R. A., Chem. Res. Toxicol. 2002, 15, 734-741.

Rao, M. R.; Tiwari, M. D.; Bellare, J. R.; Ravikanth, M., J. Org. Chem. 2011, 76, 7263-7268.
Zhang, M.; Hao, E.; Xu, Y.; Zhang, S.; Zhu, H.; Wang, Q.; Yu, C.; Jiao, L., RSC Advances 2012, 2, 11215-11218.
Zhang, M.; Hao, E.; Zhou, J.; Yu, C.; Bai, G.; Wang, F.; Jiao, L., Org. Biomol. Chem. 2012, 10, 2139-2145.
Park, G.; Tomlinson, J. T.; Melvin, M. S.; Wright, M. W.; Day, C. S.; Manderville, R. A., Org. Lett. 2003, 5, 113-116.
Crawford, S. M.; Ali, A. A.-S.; Cameron, T. S.; Thompson, A., Inorg. Chem. 2011, 50, 8207-8213.
Hong, T.; Song, H.; Li, X.; Zhang, W.; Xie, Y., RSC Adv. 2014, 4, 6133-6140.
Murakami, Y.; Matsuda, Y.; Sakata, K.; Martell, A. E., J. Chem. Soc., Dalton Trans. 1973, 1729-1734.
Smithen, D. A.; Baker, A. E. G.; Offman, M.; Crawford, S. M.; Cameron, T. S.; Thompson, A., J. Org. Chem. 2012, 77, 3439-3453.
Wallace, D. M.; Leung, S. H.; Senge, M. O.; Smith, K. M., J. Org. Chem. 1993, 58, 7245-7257.
Ptaszek, M.; McDowell, B. E.; Lindsey, J. S., J. Org. Chem. 2006, 71, 4328-4331.
García-Valverde, M.; Alfonso, I.; Quiñonero, D.; Quesada, R., J. Org. Chem. 2012, 77, 6538-6544.
Melvin, M. S.; Calcutt, M. W.; Noftle, R. E.; Manderville, R. A., Chem. Res. Toxicol. 2002, 15, 742-748.
Rastogi, S.; Marchal, E.; Uddin, I.; Groves, B.; Colpitts, J.; McFarland, S. A.; Davis, J. T.; Thompson, A., Org. Biomol. Chem. 2013, 11, 3834-3845.
Yu, C.; Jiao, L.; Tan, X.; Wang, J.; Xu, Y.; Wu, Y.; Yang, G.; Wang, Z.; Hao, E., Angew. Chem., Int. Ed. 2012, 51, 7688-7691.
Jenkins, S.; Incarvito, C. D.; Parr, J.; Wasserman, H. H., CrystEngComm 2009, 11, 242-245.
Davies, E. R., Phys. Lett. A 1974, 47, 1-2.
Holland, P. L.; Tolman, W. B., J. Am. Chem. Soc. 1999, 121, 7270-7271.
Holland, P. L.; Tolman, W. B., J. Am. Chem. Soc. 2000, 122, 6331-6332.
Pap, J. S.; Kripli, B.; Bányai, V.; Giorgi, M.; Korecz, L.; Gajda, T.; Árus, D.; Kaizer, J.; Speier, G., Inorg. Chim. Acta 2011, 376, 158-169.
Iwaizumi, M.; Kudo, T.; Kita, S., Inorg. Chem. 1986, 25, 1546-1550.
Brown, T. G.; Hoffman, B. M., Mol. Phys. 1980, 39, 1073-1109.
Mitrikas, G.; Calle, C.; Schweiger, A., Angew. Chem., Int. Ed. 2005, 44, 3301-3303.
Heinze, K.; Reinhart, A., Inorg. Chem. 2006, 45, 2695-2703.
Bailey, D. M.; Johnson, R. E.; Albertson, N. F., Org. Synth. 1971, 51, 100.
Sheldrick, G. M., Acta Cryst. 2008, A64, 112-122.
MacRae, C. F.; Bruno, I. J.; Chisholm, J. A.; Edgington, P. R.; McCabe, P.; Pidcock, E.; Rodriguez-Monge, L.; Taylor, R.; Van De Streek, J.; Wood, P. A., J. Appl. Crystallogr. 2008, 41, 466-470.
Spek, A., J. Appl. Cryst. 2003, 36, 7-13.
Van Der Sluis, P.; Spek, A., Acta Cryst. 1990, A46, 194-201.
Astashkin, A. V.; Enemark, J. H.; Raitsimring, A., Concepts Magn. Reson. Part B. Magn. Reson. Eng 2006, 29B, 125-136.
Akam et al. Disulfide-masked iron prochelators: Effects on cell death, proliferation, and hemoglobin production. Journal of Inorganic Biochemistry 180 (2018) 186-191.
Humphlett. 4-(O-arabino-tetrahydrobutyl)-4-thiazoline-2-thione. Research, 1968, 6(1), 25-33.
Humphlett. A Determination of the Structure of 4-(D-Arabino-Tetrahydroxyeiutyl)-4-Thioline-2-Thione. Carbohyd. Res., 6 (1968), 25-33.

\* cited by examiner

FIG. 1

Example 21

Example 22

Example 23

Example 24

Example 25

Example 26

Example 27

Example 28

Example 29

Example 30

Example 31

Example 32

Example 33

Example 34

Example 35

Example 36

Example 37

Example 38

Example 39

Example 40

FIG. 3

Example 57

Example 58

Example 59

Example 60

Example 61

Example 62

Example 63

Example 64

Example 65

Example 66

Example 67

Example 68

REDOX-ACTIVATED PRO-CHELATORS

CROSS REFERENCE

This application is a continuation-in-part and claims benefit of U.S. patent application Ser. No. 15/345,393, filed Nov. 7, 2016, which is a continuation and claims benefit of U.S. patent application Ser. No. 14/531,634, filed Nov. 3, 2014, now U.S. Pat. No. 9,486,423, which claims benefit of U.S. Provisional Patent Application No. 61/899,262, filed Nov. 3, 2013, the specification(s) of which is/are incorporated herein in their entirety by reference.

This application is a continuation-in-part and claims benefit to U.S. patent application Ser. No. 16/014,905, filed Jun. 21, 2018, which is a continuation-in-part of PCT Application No. PCT/US16/68061, filed Dec. 21, 2016, which claims benefit of U.S. Provisional Application No. 62/270,246, filed Dec. 21, 2015, the specification(s) of which is/are incorporated herein in their entirety by reference. U.S. patent application Ser. No. 16/014,905 is also a continuation-in-part and claims benefit of Ser. No. 15/345,393, filed Nov. 7, 2016, which is a continuation and claims benefit of U.S. patent application Ser. No. 14/531,634, filed Nov. 3, 2014, now U.S. Pat. No. 9,486,423, which claims benefit of U.S. Provisional Patent Application No. 61/899,262, filed Nov. 3, 2013, the specification(s) of which is/are incorporated herein in their entirety by reference.

STATEMENT REGARDING FEDERALLY SPONSORED RESEARCH OR DEVELOPMENT

This invention was made with government support under Grant No. R01 GM127646, awarded by NIH. The government has certain rights in the invention.

FIELD OF THE INVENTION

The present invention relates to metal ion pro-chelators, more particularly, to redox-activated pro-chelators. In some embodiments, the pro-chelators of the present invention may be useful for the treatment of conditions associated with metal ion disregulation.

BACKGROUND OF THE INVENTION

Metal ions play an important role in many biological systems. The proper concentration of certain metal ions can be crucial to the correct functioning of cells, organs, metabolic pathways or reactions in biological settings. Metal ions are regulated to provide the optimal concentrations for life and function. Various disease conditions are associated with metal ion disregulation.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

SUMMARY OF THE INVENTION

According to one embodiment, the present invention features pro-chelators which can be activated in reducing conditions so as to transform into chelators that sequester iron or another metal.

In a first embodiment, the present invention features a redox-activated pro-chelator having a formula according to Formula A-1:

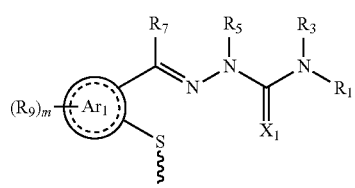

Formula A-1

In a second embodiment, the present invention features a redox activated pro-chelator having a formula according to Formula B-1, Formula B-2, Formula B-3, or Formula B-4:

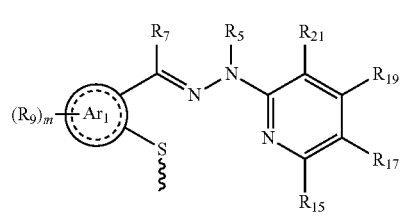

Formula B-1

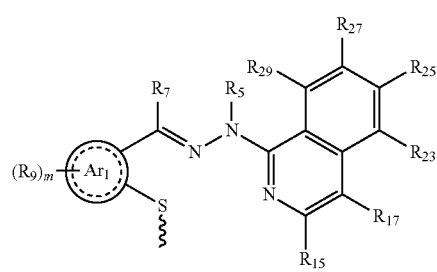

Formula B-2

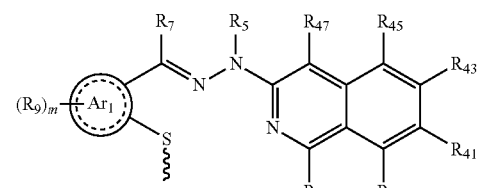

Formula B-3

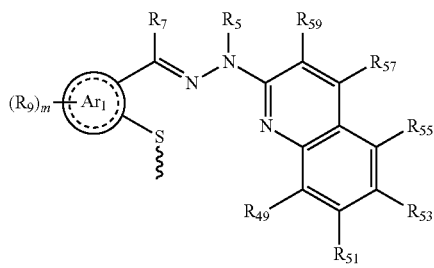

Formula B-4

In a third embodiment, the present invention features a redox activated pro-chelator having a formula according to Formula C-1:

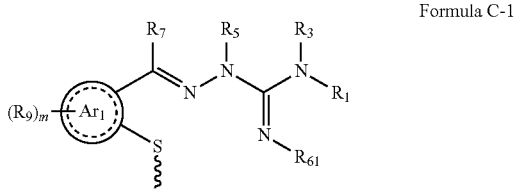

Formula C-1

In other embodiments, the above pro-chelators may be used in the treatment of a condition associated with metal ion disregulation. As a non-limiting example, the chelators of the present invention may be used in the treatment of a type of cancer such as breast cancer.

One of the unique and inventive technical features of the present invention is that the pro-chelators comprise a reducible disulfide bond. Without wishing to limit the invention to any theory or mechanism, the pro-chelators may be activated under reducing conditions to provide active metal chelators. This technical feature of the present invention advantageously pro-chelators which may be used in the in the treatment of conditions associated with metal ion disregulation. None of the presently known prior references or work has the unique inventive technical feature of the present invention.

BRIEF DESCRIPTION OF THE DRAWINGS

The features and advantages of the present invention will become apparent from a consideration of the following detailed description presented in connection with the accompanying drawings in which:

Figure 1:
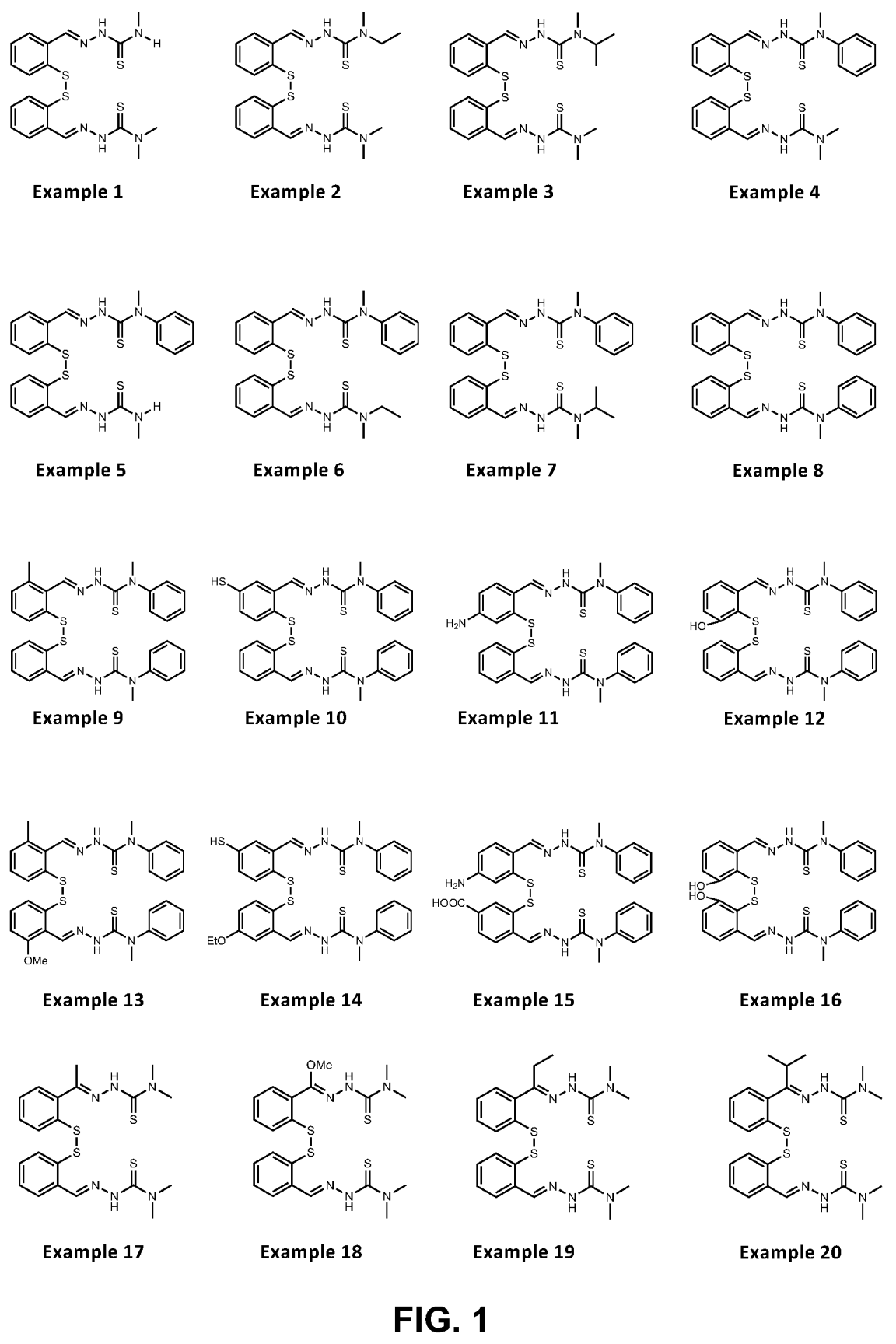

FIG. 1 shows non-limiting exemplary structures of pro-chelators of the present invention.

Figure 3:
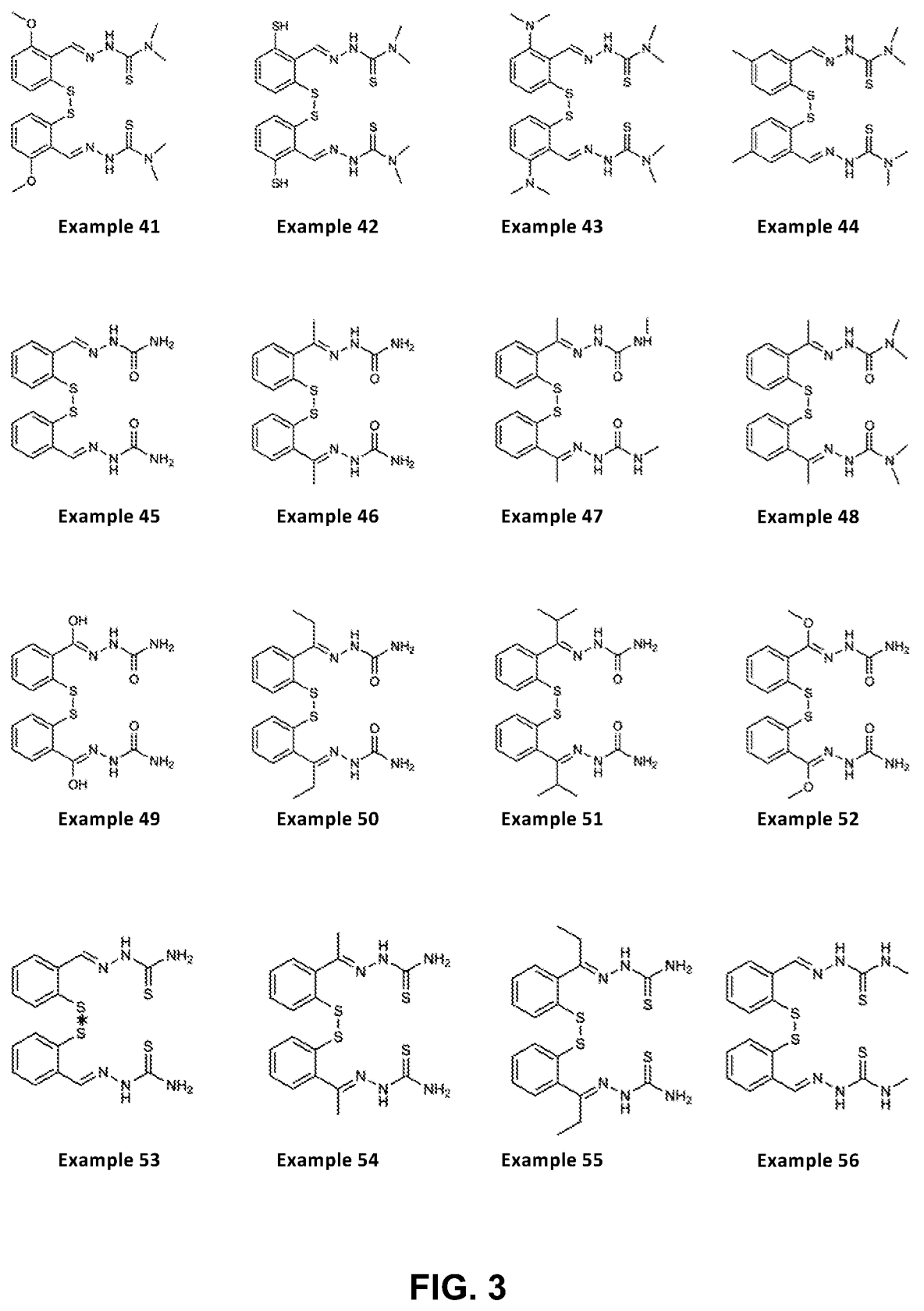

FIG. 3 shows additional non-limiting exemplary structures of pro-chelators of the present invention.

DESCRIPTION OF PREFERRED EMBODIMENTS

Figure 2:
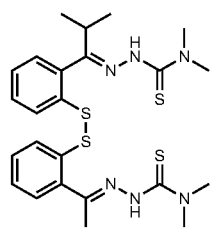
FIG. 2 shows additional non-limiting exemplary structures of pro-chelators of the present invention.
Figure 2:
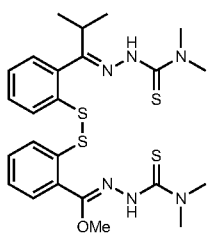
Figure 2:
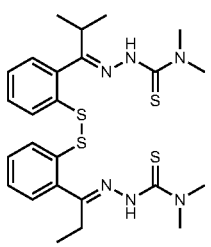
Figure 2:
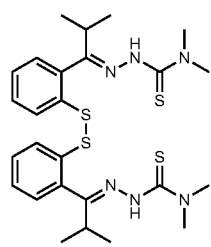
Figure 2:
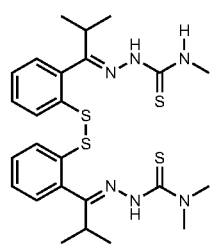
Figure 2:
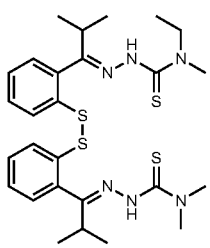
Figure 2:
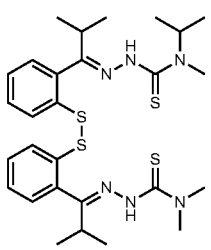
Figure 2:
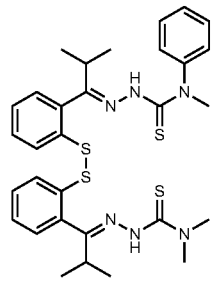
Figure 2:
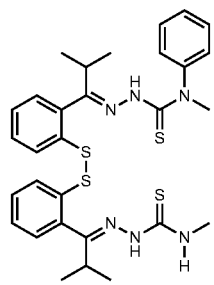
Figure 2:
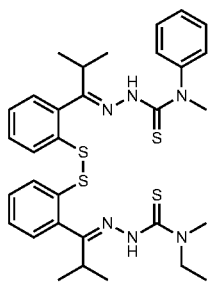
Figure 2:
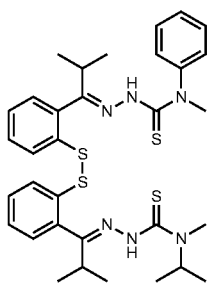
Figure 2:
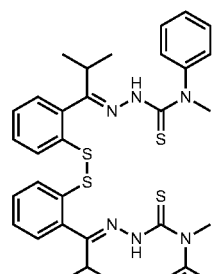
Figure 2:
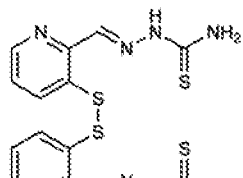
Figure 2:
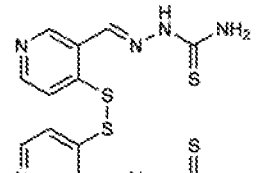
Figure 2:
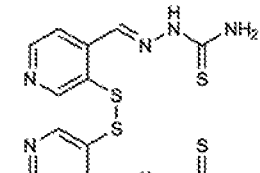
Figure 2:
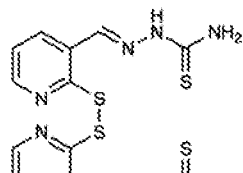
Figure 2:
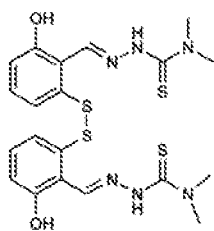
Figure 2:
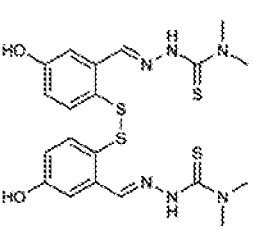
Figure 2:
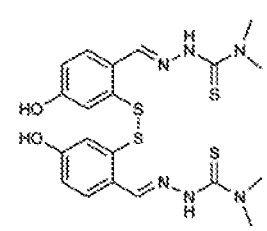
Figure 2:
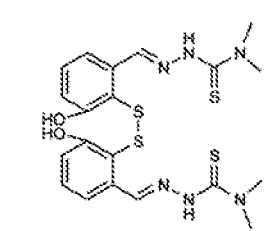
Figure 4:
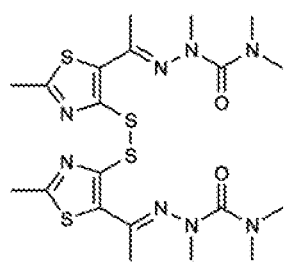
FIG. 4 shows additional non-limiting exemplary structures of pro-chelators of the present invention.
Figure 4:
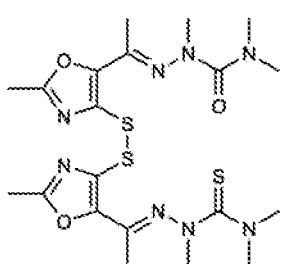
Figure 4:
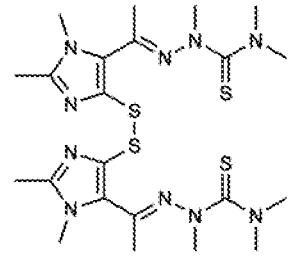
Figure 4:
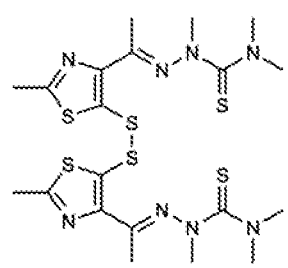
Figure 4:
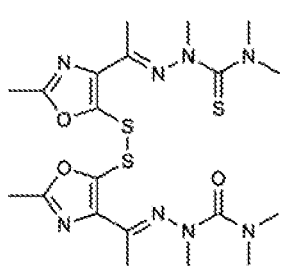
Figure 4:
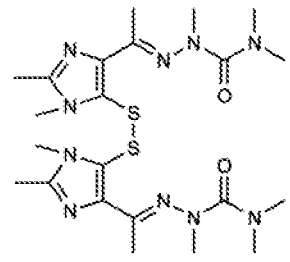
Figure 4:
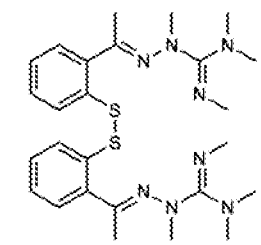
Figure 4:
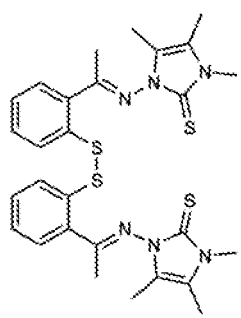
Figure 4:
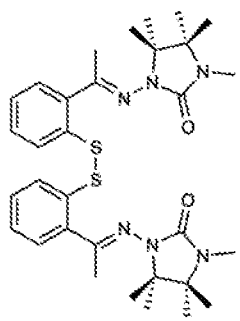
Figure 4:
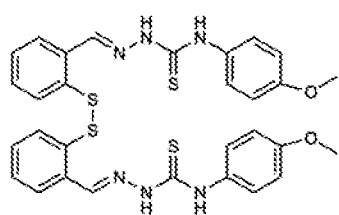
Figure 4:
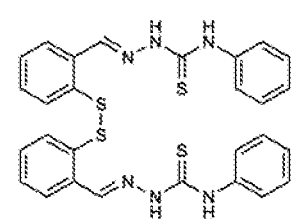
Figure 4:
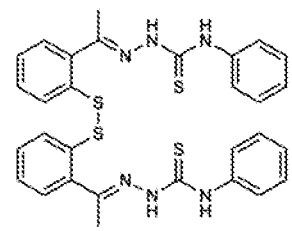

Prochelation strategies, in which the chelator is activated in response to a triggering event, increase the selectivity of biologically active chelators, and are therefore addressing a contemporary challenge in the design of chelation approaches that target conditions, such as cancer.

As used herein, the term "chelator" refers to a compound or a moiety that is capable of coordinating (or binding) a metal ion in a polydentate (e.g., coordination via two or more atoms of moieties) fashion. As such, the chelator may be referred to a polydentate ligand. The chelator may include donor atoms, such as S, N, or O, which are atoms in the chelator that bind to the metal. For example, a chelator of the present invention may be an iron chelator, which is a chelator that coordinates iron. In other embodiments the chelator may be a chelator for another metal. In some embodiments, the iron chelator may be a tridentate ligand that has three donor atoms. However, it is to be understood that chelators typically have binding affinity for more than one metal ion; therefore, the iron chelator of the present invention can also bind other types of metal ions and does not necessarily bind iron exclusively.

As used herein, the term "pro-chelators" refers to a compound or a moiety that is transformed into a chelator following activation via a chemical reaction (e.g., via reduction or with or by another compound) or by an enzyme such as a reducing enzyme. The pro-chelators described herein may comprise a disulfide bond and at least two donor atoms. For instance, the pro-chelator comprises a disulfide bond linked to a chelator that contains donor atoms. An "iron pro-chelator" is a pro-chelator that, when activated, is transformed into an iron chelator.

When describing a chemical reaction, the terms "initiating", "contacting" and "reacting" are used interchangeably herein, and refer to adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product.

As known to one of ordinary skill in the art, reducing conditions, or reducing environments, refer to conditions in which oxidative species are removed or kept at low levels to prevent oxidation. Reducing species, such as thiols or reducing peptides and enzymes, may be utilized to maintain the reducing conditions. As known to one of ordinary skill in the art, the intracellular space of a cell is a reducing environment, namely, due to the presence of reducing species and the slightly acidic conditions where the intracellular pH is about 6.8.

"Alkyl" refers to a saturated linear monovalent hydrocarbon moiety of one to twelve, typically one to six, carbon atoms or a saturated branched monovalent hydrocarbon moiety of three to twelve, typically three to six, carbon atoms. Examples of alkyl groups include, but are not limited to, methyl, ethyl, n-propyl, 2-propyl, tert-butyl, pentyl, and the like.

"Aryl" refers to a monovalent mono-, bi- or tricyclic aromatic hydrocarbon moiety of 6 to 15 ring atoms. The aryl may be optionally substituted with one or more substituents within the ring structure, referred to herein as a substituted aryl. When two or more substituents are present in an aryl group, each substituent is independently selected.

The term "heteroaryl" means a monovalent monocyclic or bicyclic aromatic moiety of 5 to 12 ring atoms containing one, two, or three ring heteroatoms selected from N, O, or S, the remaining ring atoms being C. The heteroaryl ring is optionally substituted independently with one or more substituents. Exemplary heteroaryls include, but are not limited to, pyridyl, furanyl, thiophenyl, thiazolyl, isothiazolyl, triazolyl, imidazolyl, isoxazolyl, pyrrolyl, pyrazolyl, pyrimidinyl, benzofuranyl, isobenzofuranyl, benzothiazolyl, benzoisothiazolyl, benzotriazolyl, indolyl, isoindolyl, benzoxazolyl, quinolyl, isoquinolyl, benzimidazolyl, benzisoxazolyl, benzothiophenyl, dibenzofuran, and benzodiazepin-2-one-5-yl, and the like.

The term "ion stabilizing group" refers to a moiety whose presence in the molecule increases the stability of the ion relative to the absence of such a group. One skilled in the art can readily determine whether a substituent or a moiety is an ion stabilizing group.

"Protecting group" refers to a moiety, except alkyl groups, that when attached to a reactive group in a molecule masks, reduces or prevents that reactivity. Examples of protecting groups can be found in T. W. Greene and P. G M. Wuts, *Protective Groups in Organic Synthesis*, 3$^{rd}$ edition, John Wiley & Sons, New York, 1999, and Harrison and Harrison et al., *Compendium of Synthetic Organic Methods*, Vols. 1-8 (John Wiley and Sons, 1971-1996), which are incorporated herein by reference in their entirety. Representative hydroxy protecting groups include acyl groups, benzyl and trityl ethers, tetrahydropyranyl ethers, trialkylsilyl ethers and allyl ethers. Representative amino protecting groups include, formyl, acetyl, trifluoroacetyl, benzyl, benzyloxycarbonyl (CBZ), tert-butoxycarbonyl (Boc), trimethyl silyl (TMS), 2-trimethylsilyl-ethanesulfonyl (SES), trityl and substituted trityl groups, allyloxycarbonyl, 9-fluorenylmethyloxycarbonyl (FMOC), nitro-veratryloxycarbonyl (NVOC), and the like.

Redox-Activated Iron Pro-Chelators

In some embodiments, the present invention features a redox-activated pro-chelator having a formula according to Formula A-1:

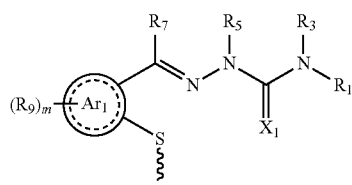

Formula A-1

In some embodiments $R_1$, $R_3$, $R_5$, and $R_7$, may each independently be H, Me, Et, Pr, i-Pr, Ph, alkyl, aryl, heteroaryl, substituted alkyl, substituted aryl, substituted heteroaryl, an electron withdrawing group, an ion stabilizing group, or an electron stabilizing group and $R_9$ is H, alkyl, aryl, alkoxy, carboxy, hydroxy, amino, phosphate, sulfonate, thiol, nitro, nitrile, halo, an electron withdrawing group, an ion stabilizing group, or an electron stabilizing group. In some other embodiments, m may be 0, 1, 2, 3, 4, 5, or 6. In still other embodiments, $X_1$ may be O or S. In further embodiments, $Ar_1$ may be aromatic, substituted aromatic, heteroaromatic, substituted heteroaromatic, phenyl, phenol, furan, thiophene, pyrrole, pyridine, imidazole, thiazole, or pyrimidine.

In one embodiment, the pro-chelator may be according to Formula A-2, Formula A-3, Formula A-4, or Formula A-5:

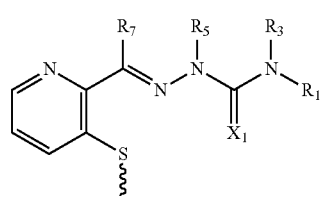

Formula A-2

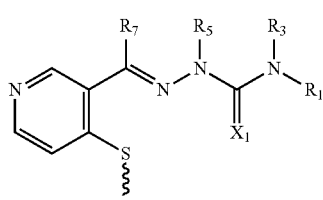

Formula A-3

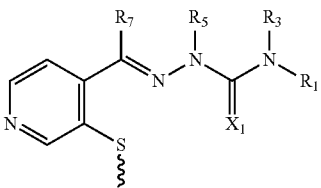

Formula A-4

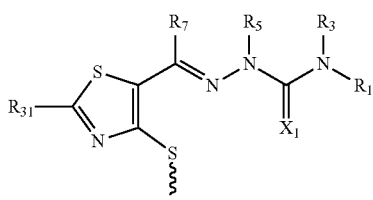

Formula A-5

In another embodiment, the pro-chelator may be according to Formula A-6, Formula A-7, Formula A-8, Formula A-9, Formula A-10 or Formula A-11:

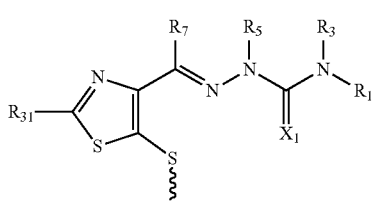

Formula A-6

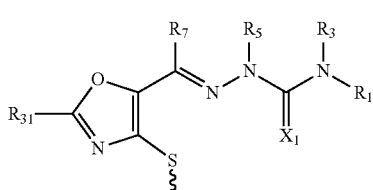

Formula A-7

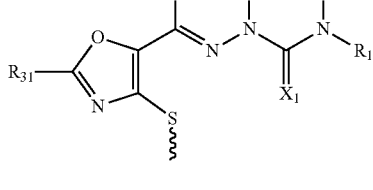

Formula A-8

Formula A-9

Formula A-10

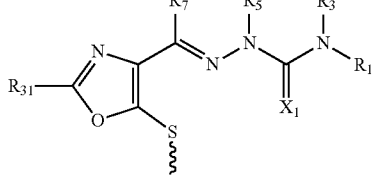

Formula A-11

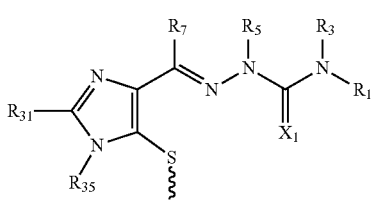

In yet another embodiment, $R_{31}$, $R_{33}$, and $R_{35}$ may each independently be H, Me, Et, Pr, i-Pr, Ph, alkyl, aryl, heteroaryl, substituted alkyl, substituted aryl, substituted heteroaryl, alkoxy, carboxy, hydroxy, amino, phosphate, sulfonate, thiol, nitro, nitrile, halo, an electron withdrawing group, an ion stabilizing group, or an electron stabilizing group. In another embodiment still, the pro-chelator may be according to Formula A-12 or Formula A-13:

Formula A-12

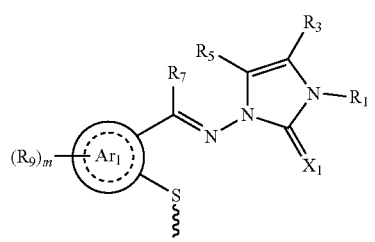

Formula A-13

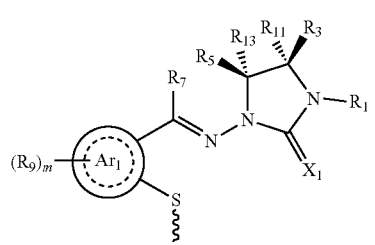

According to some embodiments, $R_{11}$, and $R_{13}$ may each independently be H, Me, Et, Pr, i-Pr, Ph, alkyl, aryl, heteroaryl, substituted alkyl, substituted aryl, substituted heteroaryl, alkoxy, carboxy, hydroxy, amino, phosphate, sulfonate, thiol, nitro, nitrile, halo, an electron withdrawing group, an ion stabilizing group, or an electron stabilizing group. According to some other embodiments, the pro-chelator may be according to Formula A-14:

Formula A-14

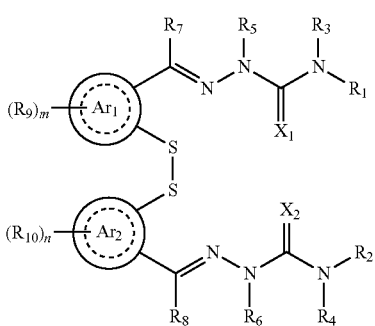

In some embodiments, $R_2$, $R_4$, $R_6$, $R_8$, and $R_{10}$ may each independently be H, Me, Et, Pr, i-Pr, Ph, alkyl, aryl, heteroaryl, substituted alkyl, substituted aryl, substituted heteroaryl, alkoxy, carboxy, hydroxy, amino, phosphate, sulfonate, thiol, nitro, nitrile, halo, an electron withdrawing group, an ion stabilizing group, or an electron stabilizing group. In some other embodiments, n may be 0, 1, 2, 3, 4, 5, or 6. According to some additional embodiments, $X_2$ may be O or S. In still other embodiments, $Ar_2$ may be aromatic, substituted aromatic, heteroaromatic, substituted heteroaromatic, phenyl, phenol, furan, thiophene, pyrrole, pyridine, imidazole, thiazole, or pyrimidine. In some selected embodiments, the pro-chelator may be according to Formula A-15, Formula A-16, Formula A-17, or Formula A-18:

Formula A-15

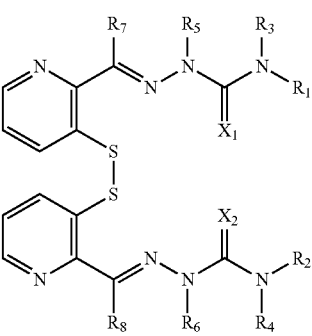

Formula A-16

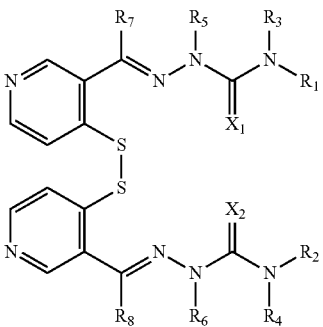

Formula A-17

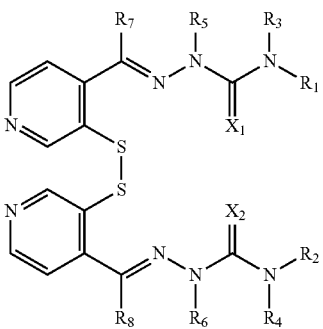

-continued

Formula A-18
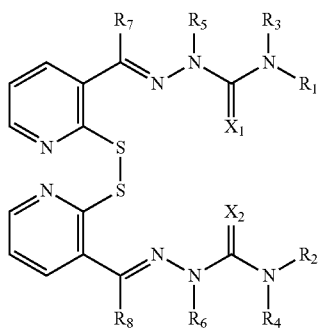

In one embodiment, the pro-chelator may be according to Formula A-19, Formula A-20, Formula A-21, Formula A-22, Formula A-23 or Formula A-24:

Formula A-19
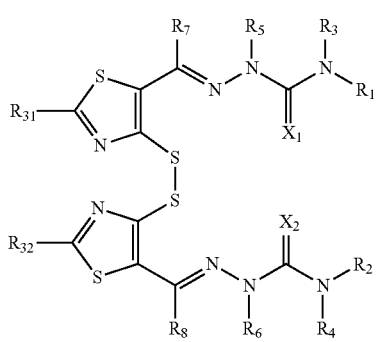

Formula A-20
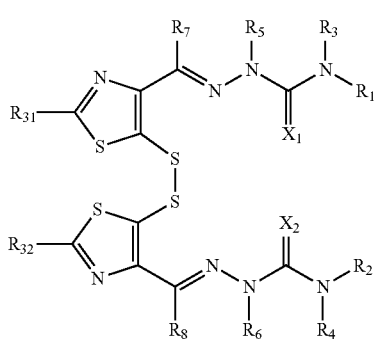

Formula A-21
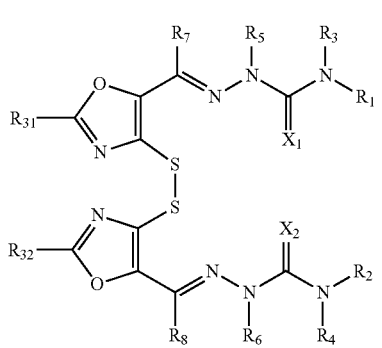

-continued

Formula A-22
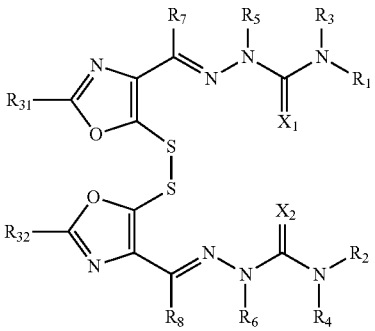

Formula A-23
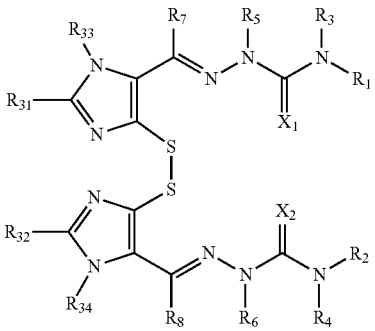

Formula A-24
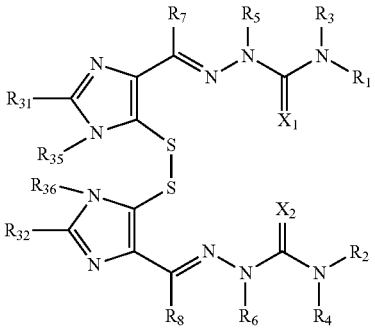

In another embodiment, $R_{31}$, $R_{32}$, $R_{35}$, and $R_{36}$ may each independently be H, Me, Et, Pr, i-Pr, Ph, alkyl, aryl, heteroaryl, substituted alkyl, substituted aryl, substituted heteroaryl, alkoxy, carboxy, hydroxy, amino, phosphate, sulfonate, thiol, nitro, nitrile, halo, an electron withdrawing group, an ion stabilizing group, or an electron stabilizing group. In still another embodiment, the pro-chelator may be according to Formula A-25 or Formula A-26:

Formula A-25
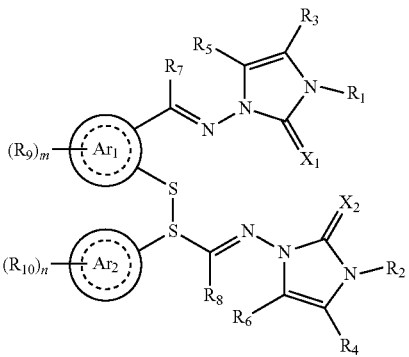

Formula A-26

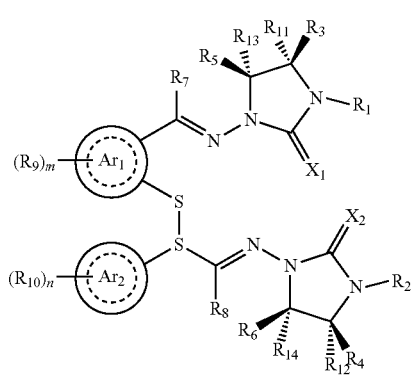

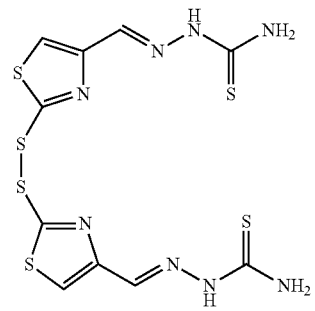

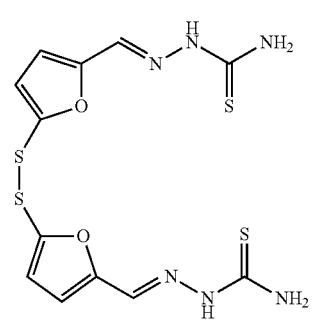

In a preferred embodiment $R_{11}$, $R_{12}$, $R_{13}$, and $R_{14}$ may each independently be H, Me, Et, Pr, i-Pr, Ph, alkyl, aryl, heteroaryl, substituted alkyl, substituted aryl, substituted heteroaryl, alkoxy, carboxy, hydroxy, amino, phosphate, sulfonate, thiol, nitro, nitrile, halo, an electron withdrawing group, an ion stabilizing group, or an electron stabilizing group.

In another preferred embodiment, the pro-chelator may be according to Formula A-27 or Formula A-28:

Formula A-27

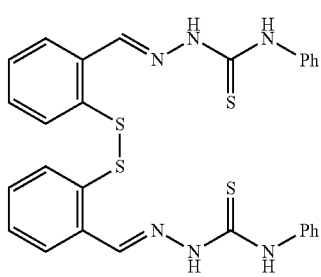

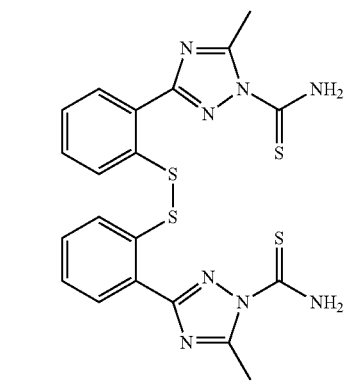

Formula A-28

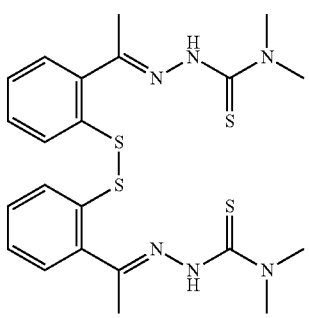

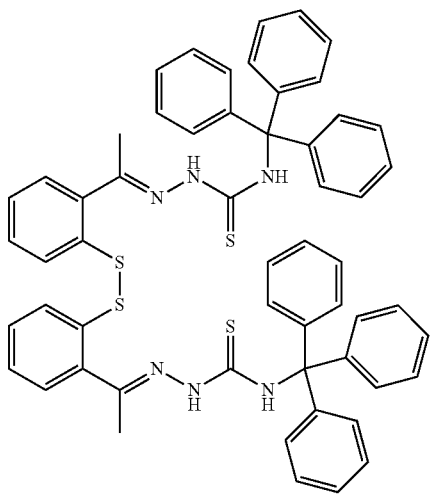

The R groups are selected such that the following structures are not included as possible embodiments:

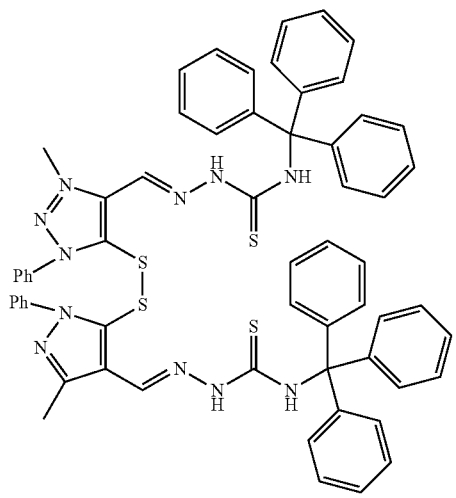

For example, when $Ar_1$ and $Ar_2$ are thiazoles or furans, $R_1$, $R_2$, $R_3$, $R_4$, $R_5$, $R_6$, $R_7$ and $R_8$ may not all be H. When $Ar_1$ and $Ar_2$ are aryl rings and $R_1$, $R_2$, $R_3$, and $R_4$ are each H, $R_5$, $R_6$, $R_7$ and $R_8$ may not form triazoles. When $Ar_1$ and $Ar_2$ are aryl rings and $R_1$, $R_2$, $R_5$, and $R_6$ are each H, $R_3$ and $R_4$ may not form triphenylmethyl. When $Ar_1$ and $Ar_2$ are substituted pyrazole rings and $R_1$, $R_2$, $R_5$, and $R_6$ are each H, $R_3$ and $R_4$ may not form triphenylmethyl.

In an embodiment, the present invention may feature a redox activated pro-chelator having a formula according to Formula B-1, Formula B-2, Formula B-3, or Formula B-4:

Formula B-1

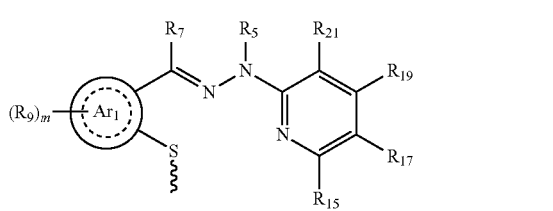

Formula B-2

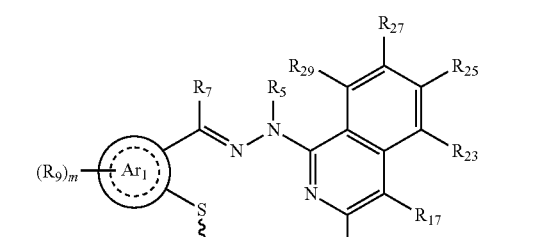

Formula B-3

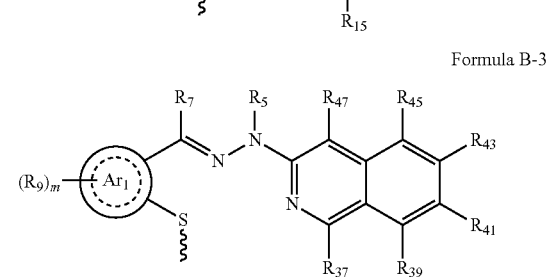

Formula B-4

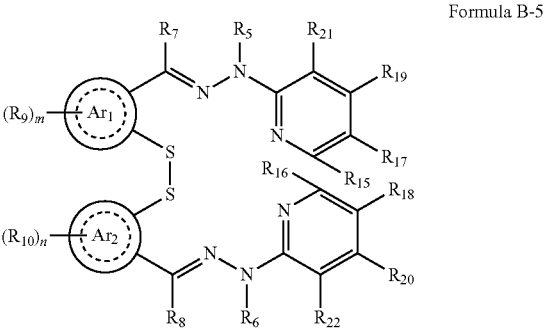

In another embodiment, $R_5$, $R_7$, $R_9$, $R_{15}$, $R_{17}$, $R_{19}$, $R_{21}$, $R_{23}$, $R_{25}$, $R_{27}$, $R_{29}$, $R_{37}$, $R_{39}$, $R_{41}$, $R_{43}$, $R_{45}$, $R_{47}$, $R_{49}$, $R_{51}$, $R_{53}$, $R_{55}$, $R_{57}$, and $R_{59}$ may each independently be H, Me, Et, Pr, i-Pr, Ph, alkyl, aryl, heteroaryl, substituted alkyl, substituted aryl, substituted heteroaryl, alkoxy, carboxy, hydroxy, amino, phosphate, sulfonate, thiol, nitro, nitrile, halo, an electron withdrawing group, an ion stabilizing group, or an electron stabilizing group. In yet another embodiment m may be 0, 1, 2, 3, 4, 5, or 6. In still another embodiment, $Ar_1$ may be aromatic, substituted aromatic, heteroaromatic, substituted heteroaromatic, phenyl, phenol, furan, thiophene, pyrrole, pyridine, imidazole, thiazole, or pyrimidine. According to some embodiments, the pro-chelator may be according to Formula B-5:

Formula B-5

In some additional embodiments, $R_6$, $R_8$, $R_{10}$, $R_{16}$, $R_{18}$, $R_{20}$, and $R_{22}$ may each independently be H, Me, Et, Pr, i-Pr, Ph, alkyl, aryl, heteroaryl, substituted alkyl, substituted aryl, substituted heteroaryl, alkoxy, carboxy, hydroxy, amino, phosphate, sulfonate, thiol, nitro, nitrile, halo, an electron withdrawing group, an ion stabilizing group, or an electron stabilizing group. In some other additional embodiments, n may be 0, 1, 2, 3, 4, 5, or 6. In still other additional embodiments, $Ar_2$ may be aromatic, substituted aromatic, heteroaromatic, substituted heteroaromatic, phenyl, phenol, furan, thiophene, pyrrole, pyridine, imidazole, thiazole, or pyrimidine. In selected embodiments, the pro-chelator may be according to Formula B-6:

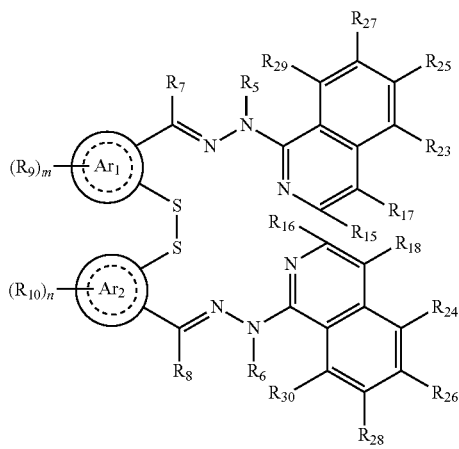

Formula B-6

In one embodiment, $R_6$, $R_8$, $R_{10}$, $R_{16}$, $R_{18}$, $R_{24}$, $R_{26}$, $R_{28}$ and $R_{30}$ may each independently be H, Me, Et, Pr, i-Pr, Ph, alkyl, aryl, heteroaryl, substituted alkyl, substituted aryl, substituted heteroaryl, alkoxy, carboxy, hydroxy, amino, phosphate, sulfonate, thiol, nitro, nitrile, halo, an electron withdrawing group, an ion stabilizing group, or an electron stabilizing group. In other embodiments, n may be 0, 1, 2, 3, 4, 5, or 6. In still other embodiments, $Ar_2$ may be aromatic, substituted aromatic, heteroaromatic, substituted heteroaromatic, phenyl, phenol, furan, thiophene, pyrrole, pyridine, imidazole, thiazole, or pyrimidine. In still other embodiments, the pro-chelator may be according to Formula B-7:

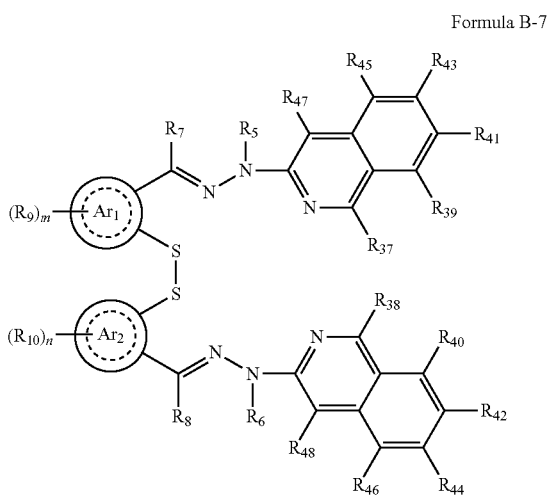

Formula B-7

In selected embodiments, $R_6$, $R_8$, $R_{10}$, $R_{38}$, $R_{40}$, $R_{42}$, $R_{44}$, $R_{46}$ and $R_{48}$ may each independently be H, Me, Et, Pr, i-Pr, Ph, alkyl, aryl, heteroaryl, substituted alkyl, substituted aryl, substituted heteroaryl, alkoxy, carboxy, hydroxy, amino, phosphate, sulfonate, thiol, nitro, nitrile, halo, an electron withdrawing group, an ion stabilizing group, or an electron stabilizing group. In other selected embodiments, n may be 0, 1, 2, 3, 4, 5, or 6. In still other embodiments, $Ar_2$ may be aromatic, substituted aromatic, heteroaromatic, substituted heteroaromatic, phenyl, phenol, furan, thiophene, pyrrole, pyridine, imidazole, thiazole, or pyrimidine. In yet other embodiments, the pro-chelator may be according to Formula B-8:

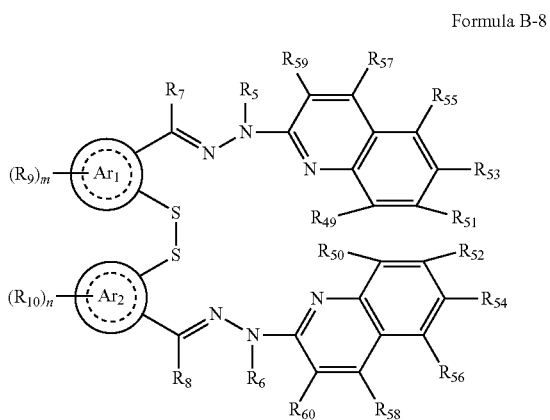

Formula B-8

According to one selected embodiment, $R_6$, $R_8$, $R_{10}$, $R_{50}$, $R_{52}$, $R_{54}$, $R_{56}$, $R_{58}$ and $R_{60}$ may each independently be H, Me, Et, Pr, i-Pr, Ph, alkyl, aryl, heteroaryl, substituted alkyl, substituted aryl, substituted heteroaryl, alkoxy, carboxy, hydroxy, amino, phosphate, sulfonate, thiol, nitro, nitrile, halo, an electron withdrawing group, an ion stabilizing group, or an electron stabilizing group. According to another selected embodiment, n may be 0, 1, 2, 3, 4, 5, or 6. According to yet another selected embodiment, $Ar_2$ may be aromatic, substituted aromatic, heteroaromatic, substituted heteroaromatic, phenyl, phenol, furan, thiophene, pyrrole, pyridine, imidazole, thiazole, or pyrimidine.

In a preferred embodiment, the present invention may feature a redox activated pro-chelator having a formula according to Formula C-1:

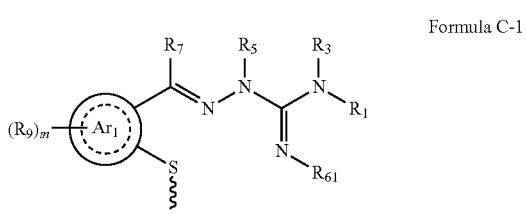

Formula C-1

In one embodiment, $R_1$, $R_3$, $R_5$, $R_7$, $R_9$, and $R_{61}$ may each independently be H, Me, Et, Pr, i-Pr, Ph, alkyl, aryl, heteroaryl, substituted alkyl, substituted aryl, substituted heteroaryl, alkoxy, carboxy, hydroxy, amino, phosphate, sulfonate, thiol, nitro, nitrile, halo, an electron withdrawing group, an ion stabilizing group, or an electron stabilizing group. In another embodiment, m may be 0, 1, 2, 3, 4, 5, or 6. In still another embodiment, $Ar_1$ may be aromatic, substituted aromatic, heteroaromatic, substituted heteroaromatic, phenyl, phenol, furan, thiophene, pyrrole, pyridine, imidazole, thiazole, or pyrimidine. In yet another embodiment, the pro-chelator may be according to Formula C-2:

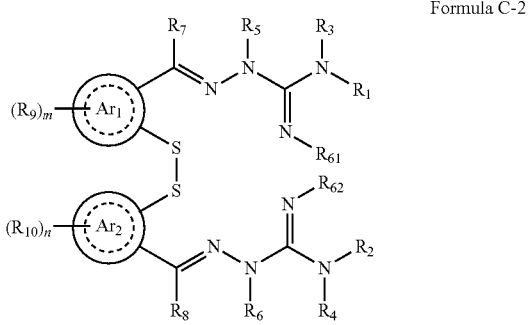

Formula C-2

In some embodiments, $R_2$, $R_4$, $R_6$, $R_8$, $R_{10}$, and $R_{62}$ may each independently be H, Me, Et, Pr, i-Pr, Ph, alkyl, aryl, heteroaryl, substituted alkyl, substituted aryl, substituted heteroaryl, alkoxy, carboxy, hydroxy, amino, phosphate, sulfonate, thiol, nitro, nitrile, halo, an electron withdrawing group, an ion stabilizing group, or an electron stabilizing group. In some other embodiments n may be 0, 1, 2, 3, 4, 5, or 6. In still other embodiments, $Ar_2$ may be aromatic, substituted aromatic, heteroaromatic, substituted heteroaromatic, phenyl, phenol, furan, thiophene, pyrrole, pyridine, imidazole, thiazole, or pyrimidine.

In selected embodiments, the redox-activated pro-chelators may be activated in reducing conditions. Chelators may be released upon reduction of the disulfide bond. The reduced species may be tridentate iron chelators forming complexes of 2:1 ligand-to-metal stoichiometry. Magnetic measurements and X-ray crystallographic data on the resulting iron complexes indicate that these chelators stabilize iron centers as low-spin Fe(III) species. The present invention is not limited to chelators that stabilize iron centers as low-spin Fe(III) species.

In some embodiments, pro-chelators of the present invention are reduced at half-cell potentials between −160 and −220 mV (vs SHE at 25° C.). In some embodiments, compounds of the invention are reduced at half-cell potentials of about −150 mV or lower, e.g., −160 mV or lower, e.g., −180 mV or lower, e.g., about −200 mV or lower. The present invention is not limited to the aforementioned reducing conditions.

Note that in some embodiments, the pro-chelator comprises a thiosemicarbazone. However, the present invention is not limited to thiosemicarbazones as any appropriate chelating agent may be use in lieu of the thiosemicarbazone. Other examples include, but are not limited to, semicarbazone, aroylhydrazone, desferrioxamine (DFO), deferiprone (DFP), hydroxypyridinone, deferasirox (DFX), desferrithiocin (DFT), or analogs thereof. In some embodiments, the thiosemicarbazone scaffold may be further modified.

Methods of Use

"A therapeutically effective amount" means the amount of a compound that, when administered to a mammal for treating a disease, is sufficient to effect such treatment for the disease. The "therapeutically effective amount" will vary depending on the compound, the disease and its severity and the age, weight, etc., of the mammal to be treated.

"Treating" or "treatment" of a disease includes: (1) preventing the disease, i.e., causing the clinical symptoms of the disease not to develop in a mammal that may be exposed to or predisposed to the disease but does not yet experience or display symptoms of the disease; (2) inhibiting the disease, i.e., arresting or reducing the development of the disease or its clinical symptoms; or (3) relieving the disease, i.e., causing regression of the disease or its clinical symptoms.

According to some embodiments, the compounds described herein may be use in methods of inhibiting proliferation of a cancer cell. In one embodiment, the method may comprise introducing to the cancer cell any one of the compounds. Upon reduction of the disulfide bond, the compound can release high-affinity chelators, which can sequester iron, thereby depriving the cell of iron and inhibiting its proliferation.

The present invention also features methods of treating a clinical condition associated with an iron dysregulation in a subject in need of such treatment. In one embodiment, the method may comprise administering to the subject a therapeutically effective amount of any of the compounds comprising a pro-chelator as described herein. In some embodiments, the clinical condition is a cancer, however the present invention is not limited to cancer and the clinical condition may be any condition that is associated with iron dysregulation in a cell. Without wishing to limit the invention to a particular theory or mechanism, the pro-chelator compound, when administered to the subject, can release high-affinity chelators upon reduction of the disulfide bond. The high-affinity chelators can sequester iron, thereby treating the iron dysregulation condition.

The present invention shows that disulfide-based pro-chelation strategies offer viable options for targeting of intracellular metal ions upon preferential uptake by cells presenting overexpression of glucose transporters. In addition to colorectal cancer, potential applications of this approach are relevant to several other human cancer phenotypes, including breast, pancreatic and lung carcinomas.

According to other embodiments, the present invention also features methods of increasing water solubility of an iron pro-chelator (e.g., a thiosemicarbazone or other appropriate pro-chelator). In some embodiments, the method comprises conjugating a carbohydrate moiety or a derivative thereof to an iron chelator, thereby producing a glycoconjugated pro-chelator (e.g., a glycoconjugated pro-chelator according to the present invention). The carbohydrate moiety and iron chelator utilized in this method may be according to any of the carbohydrate moieties and iron chelators described herein. Without wishing to limit the invention to a particular theory or mechanism, the carbohydrate moiety can increase water solubility of the pro-chelator.

Administration and Pharmaceutical Composition

In some embodiments, the present invention features pharmaceutical compositions comprising at least one pro-chelator compound of the invention, or an individual isomer, racemic or non-racemic mixture of isomers or a pharmaceutically acceptable salt or solvate thereof, together with at least one pharmaceutically acceptable carrier, and optionally other therapeutic and/or prophylactic ingredients.

"Pharmaceutically acceptable carrier" refers to a carrier that is useful in preparing a pharmaceutical composition that is generally safe, non-toxic and neither biologically nor otherwise undesirable, and that is acceptable for veterinary use as well as human pharmaceutical use.

"Pharmaceutically acceptable salt" of a compound means a salt that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1 carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

In some embodiments, the compounds of the invention are administered in a therapeutically effective amount by any of the accepted modes of administration for agents that serve similar utilities. One of ordinary skill in the art of treating such diseases is typically able, without undue experimentation and in reliance upon personal knowledge and the disclosure of this application, to ascertain a therapeutically effective amount of the compounds of the invention.

In some embodiments, compounds of the invention are administered as pharmaceutical formulations including those suitable for oral (including buccal and sub-lingual), rectal, nasal, topical, pulmonary, vaginal, or parenteral (including intramuscular, intraarterial, intrathecal, subcutaneous and intravenous) administration or in a form suitable for administration by inhalation or insufflation.

In some embodiments, a compound or compounds of the invention, together with one or more conventional adjuvants, carriers, or diluents, can be placed into the form of pharmaceutical compositions and unit dosages. In some embodiments, the pharmaceutical compositions and unit dosage forms can be comprised of conventional ingredients in conventional proportions, with or without additional active compounds or principles, and the unit dosage forms can contain any suitable effective amount of the active ingredient commensurate with the intended daily dosage range to be employed. In some embodiments, the pharmaceutical compositions can be employed as solids, such as tablets or filled capsules, semisolids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use.

In some embodiments, the compounds of the invention can be formulated in a wide variety of oral administration dosage forms. The pharmaceutical compositions and dosage forms may comprise a compound or compounds of the invention or pharmaceutically acceptable salts thereof as the active component. In some embodiments, the pharmaceutically acceptable carriers can be either solid or liquid. Solid form preparations include powders, tablets, pills, capsules, cachets, suppositories, and dispersible granules. A solid carrier may be one or more substances which can also act as diluents, flavoring agents, solubilizers, lubricants, suspending agents, binders, preservatives, tablet disintegrating agents, or an encapsulating material. Suitable carriers may include but are not limited to magnesium carbonate, magnesium stearate, talc, sugar, lactose, pectin, dextrin, starch, gelatine, tragacanth, methylcellulose, sodium carboxymethylcellulose, a low melting wax, cocoa butter, and the like. The term "preparation" is intended to include the formulation of the active compound with encapsulating material as carrier, providing a capsule in which the active component, with or without carriers, is surrounded by a carrier, which is in association with it. Similarly, cachets and lozenges are included. Tablets, powders, capsules, pills, cachets, and lozenges can be as solid forms suitable for oral administration.

Other forms suitable for oral administration include liquid form preparations including emulsions, syrups, elixirs, aqueous solutions, aqueous suspensions, or solid form preparations which are intended to be converted shortly before use to liquid form preparations. Emulsions can be prepared in solutions, for example, in aqueous propylene glycol solutions or may contain emulsifying agents, for example, such as lecithin, sorbitan monooleate, or acacia. Aqueous solutions can be prepared by dissolving the active component in water and adding suitable colorants, flavors, stabilizers, and thickening agents. Aqueous suspensions can be prepared by dispersing the finely divided active component in water with viscous material, such as natural or synthetic gums, resins, methylcellulose, sodium carboxymethylcellulose, and other well-known suspending agents. Solid form preparations include solutions, suspensions, and emulsions, and can contain, in addition to the active component, colorants, flavors, stabilizers, buffers, artificial and natural sweeteners, dispersants, thickeners, solubilizing agents, and the like.

In some embodiments, the compounds of the invention can also be formulated for parenteral administration (e.g., by injection, for example bolus injection or continuous infusion) and can be presented in unit dose form in ampoules, pre-filled syringes, small volume infusion or in multi-dose containers with an added preservative. The compositions can take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and can contain formulatory agents such as preserving, wetting, emulsifying or suspending, stabilizing and/or dispersing agents. Alternatively, the active ingredient can be in powder form, obtained by aseptic isolation of sterile solid or by lyophilization from solution for constitution before use with a suitable vehicle, e.g., sterile, pyrogen-free water. In some embodiments, the compounds of the invention can be formulated for topical administration to the epidermis as ointments, creams or lotions, or as a transdermal patch. Ointments and creams can, for example, be formulated with an aqueous or oily base with the addition of suitable thickening and/or gelling agents. Lotions can be formulated with an aqueous or oily base and will in general also contain one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth; pastilles comprising the active ingredient in an inert base such as gelatine and glycerine or sucrose and acacia; and mouthwashes comprising the active ingredient in a suitable liquid carrier.

In some embodiments, the compounds of the invention can be formulated for administration as suppositories. For example, a low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify. In some embodiments, the compounds of the invention can also be formulated for vaginal administration. Pessaries, tampons, creams, gels, pastes, foams or sprays containing in addition to the active ingredient such carriers as are known in the art to be appropriate. In some embodiments, the compounds of the invention can be formulated for nasal administration. The solutions or suspensions are applied directly to the nasal cavity by conventional means, for example, with a dropper, pipette or spray. The formulations can be provided in a single or multidose form. In the latter case of a dropper or pipette, this can be achieved by the patient administering an appropriate, predetermined volume of the solution or suspension. In the case of a spray, this can be achieved for example by means of a metering atomizing spray pump.

As used herein, the term "about" refers to plus or minus 10% of the referenced number.

Various modifications of the invention, in addition to those described herein, will be apparent to those skilled in the art from the foregoing description. Such modifications are also intended to fall within the scope of the appended claims. Each reference cited in the present application is incorporated herein by reference in its entirety.

Although it has been shown and described the preferred embodiment of the present invention, it will be readily apparent to those skilled in the art that modifications may be made thereto which do not exceed the scope of the appended claims. Therefore, the scope of the invention is only to be limited by the following claims. Reference numbers recited in the claims are exemplary and for ease of review by the patent office only, and are not limiting in any way. In some embodiments, the figures presented in this patent application are drawn to scale, including the angles, ratios of dimensions, etc. In some embodiments, the figures are representative only and the claims are not limited by the dimensions of the figures. In some embodiments, descriptions of the inventions described herein using the phrase "comprising" includes embodiments that could be described as "consisting of", and as such the written description requirement for claiming one or more embodiments of the present invention using the phrase "consisting of" is met.

What is claimed is:

1. A redox-activated pro-chelator having a formula according to Formula A-1, Formula A-12, or Formula A-13:

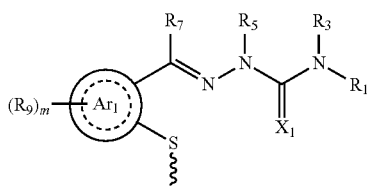

Formula A-1

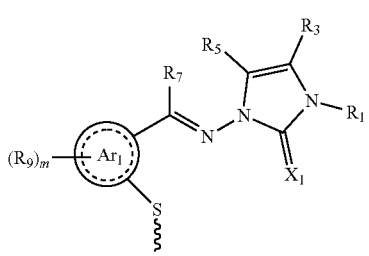

Formula A-12

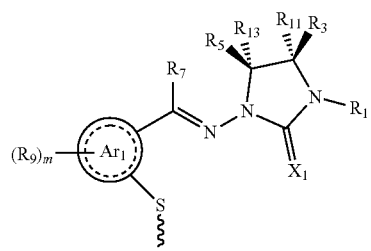

Formula A-13 wherein $R_1$, $R_3$, $R_5$, $R_7$, $R_{11}$, and $R_{13}$ are each independently H, Me, Et, Pr, i-Pr, Ph, alkyl, aryl, heteroaryl, substituted alkyl, substituted aryl, or substituted heteroaryl and $R_9$ is H, alkyl, aryl, alkoxy, carboxy, hydroxy, amino, phosphate, sulfonate, thiol, nitro, nitrile, or halo;

wherein S is bound to a first carbon on $Ar_1$;

wherein

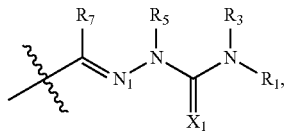

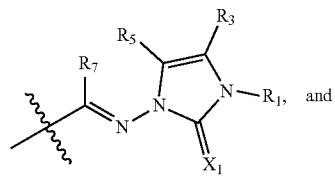
, and

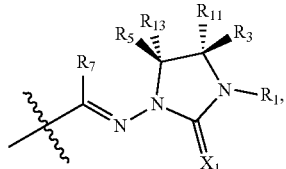
, are bound to another carbon adjacent to the first carbon on $Ar_1$, wherein m is 0, 1, 2, 3, 4, 5, or 6;

wherein $X_1$ is O or S;

wherein $Ar_1$ is aromatic, substituted aromatic, heteroaromatic, substituted heteroaromatic, phenyl, phenol, furan, thiophene, pyrrole, pyridine, imidazole, thiazole, or pyrimidine;

wherein the pro-chelator comprises a disulfide bond; and
wherein Formula A-1 excludes

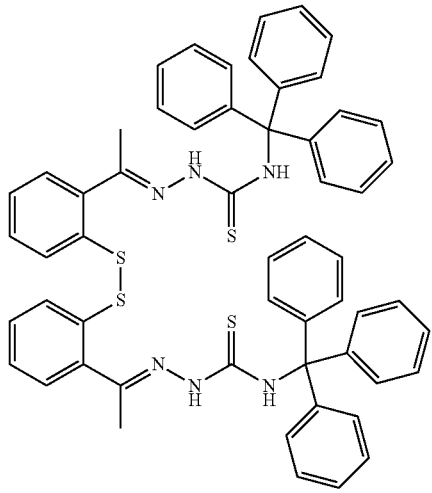

and

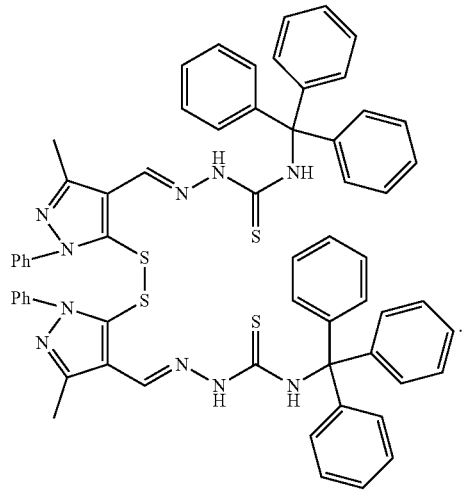

2. The pro-chelator of claim 1, wherein the pro-chelator is according to Formula A-2, Formula A-3, Formula A-4, or Formula A-5:

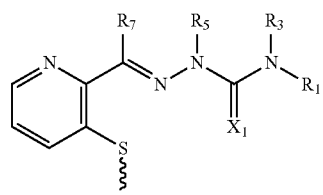

Formula A-2

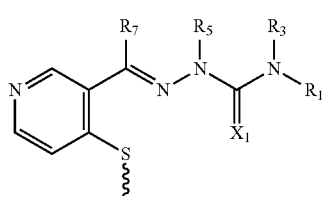

Formula A-3

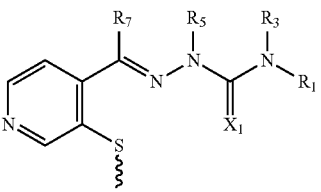

Formula A-4

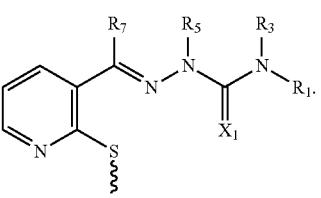

Formula A-5

3. The pro-chelator of claim 1, wherein the pro-chelator is according to Formula A-6, Formula A7, Formula A-8, Formula A-9, Formula A-10 or Formula A-11:

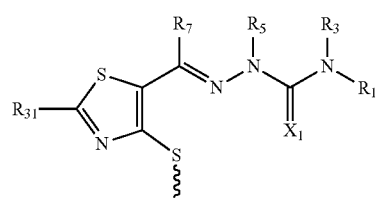

Formula A-6

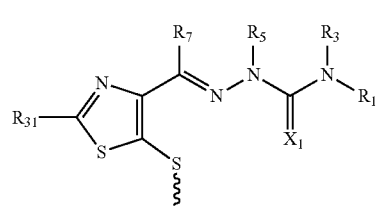

Formula A-7

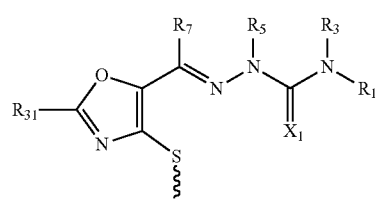

Formula A-8

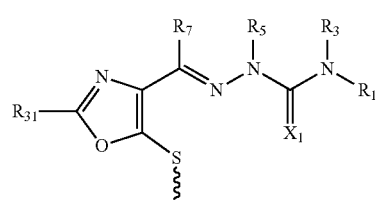

Formula A-9

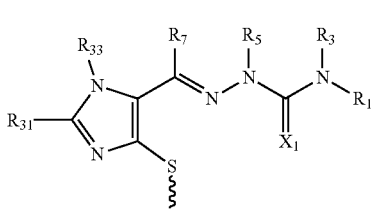

Formula A-10

Formula A-11

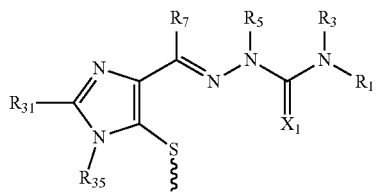

wherein $R_{31}$, $R_{33}$, and $R_{35}$ are each independently H, Me, Et, Pr, i-Pr, Ph, alkyl, aryl, alkoxy, carboxy, hydroxy, amino, phosphate, sulfonate, thiol, nitro, nitrile, or halo.

4. The pro-chelator of claim 1, wherein the pro-chelator is according to Formula A-14, Formula A-25, or Formula A-26:

Formula A-14

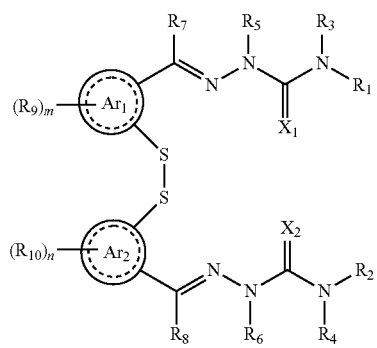

Formula A-25

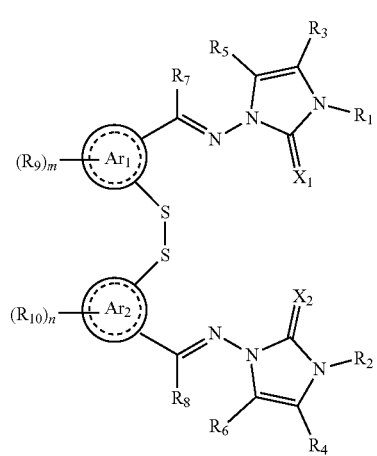

Formula A-26

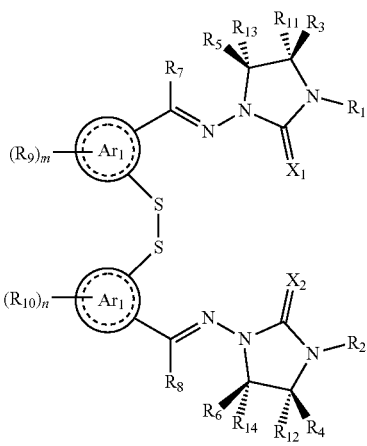

wherein $R_2$, $R_4$, $R_6$, $R_8$, $R_{12}$, and $R_{14}$ are each independently H, Me, Et, Pr, i-Pr, Ph, alkyl, aryl, heteroaryl, substituted alkyl, substituted aryl, or substituted heteroaryl and $R_{10}$ is H, alkyl, aryl, alkoxy, carboxy, hydroxy, amino, phosphate, sulfonate, thiol, nitro, nitrile, or halo;

wherein n is 0, 1, 2, 3, 4, 5, or 6;

wherein $X_2$ is O or S; and wherein $Ar_2$ is aromatic, substituted aromatic, heteroaromatic, substituted heteroaromatic, phenyl, phenol, furan, thiophene, pyrrole, pyridine, imidazole, thiazole, or pyrimidine.

5. The pro-chelator of claim 4, wherein the pro-chelator is according to Formula A-15, Formula A-16, Formula A-17, or Formula A-18:

Formula A-15

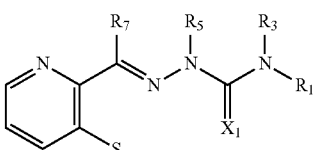

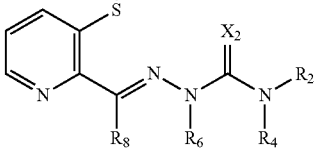

Formula A-16

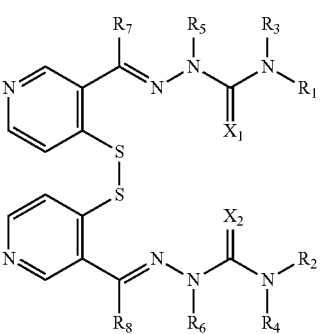

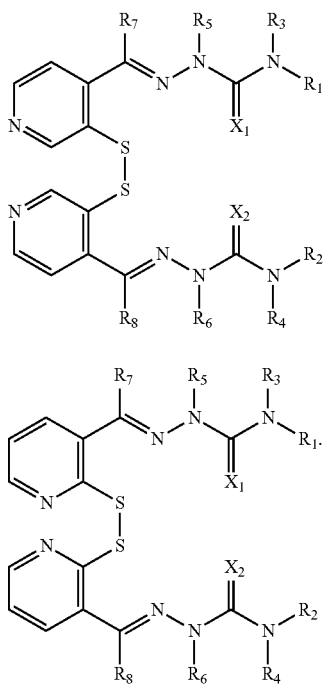

Formula A-17

Formula A-18

6. The po-chelator of claim 4, wherein the pro-chelator is according to Formula A19, Formula A-20, Formula A-21, Formula A22, Formula A-23 or Formula A-24:

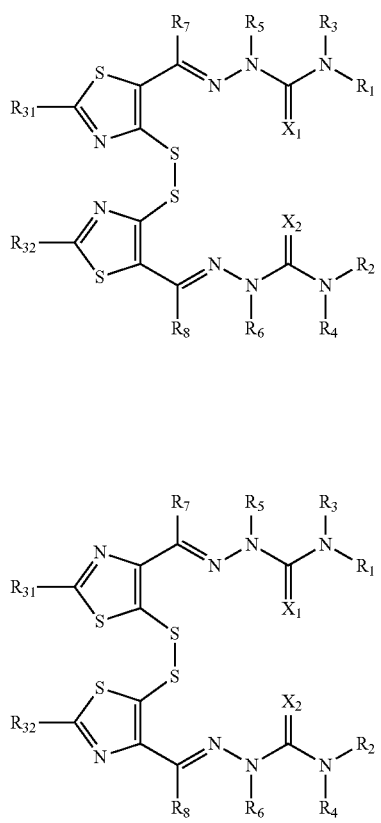

Formula A-19

Formula A-20

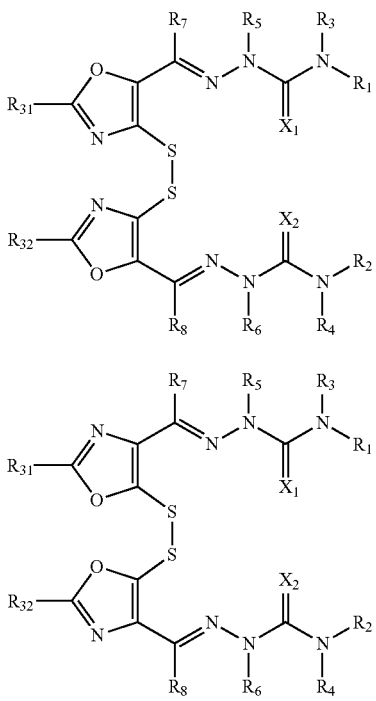

Formula A-21

Formula A-22

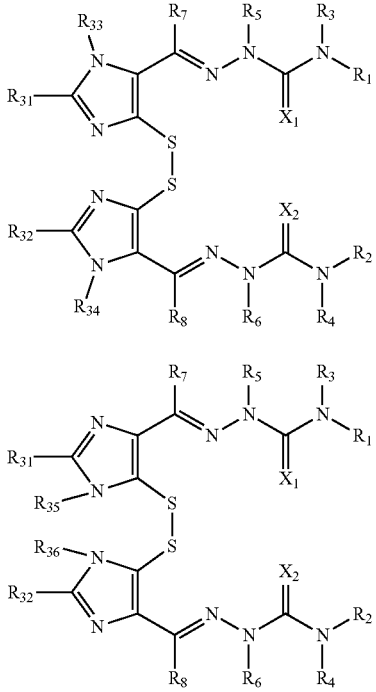

Formula A-23

Formula A-24 wherein $R_{31}$, $R_{32}$, $R_{33}$, $R_{34}$, $R_{35}$, and $R_{36}$ are each independently H, alkyl, aryl, alkoxy, carboxy, hydroxy, amino, phosphate, sulfonate, thiol, nitro, nitrile, or halo.

7. A redox-activated pro-chelator having a formula according to Formula A-27:

Formula A-27

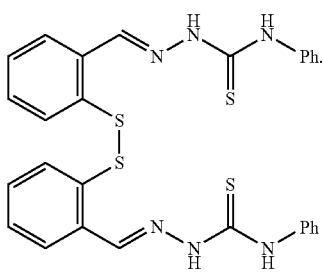

8. The pro-chelator of claim 1, wherein the pro-chelator is according to Formula A-28:

Formula A-28

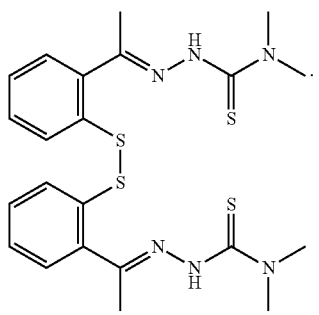

9. A redox activated pro-chelator having a formula according to Formula B-1, Formula B-2, Formula B-3, or Formula B-4:

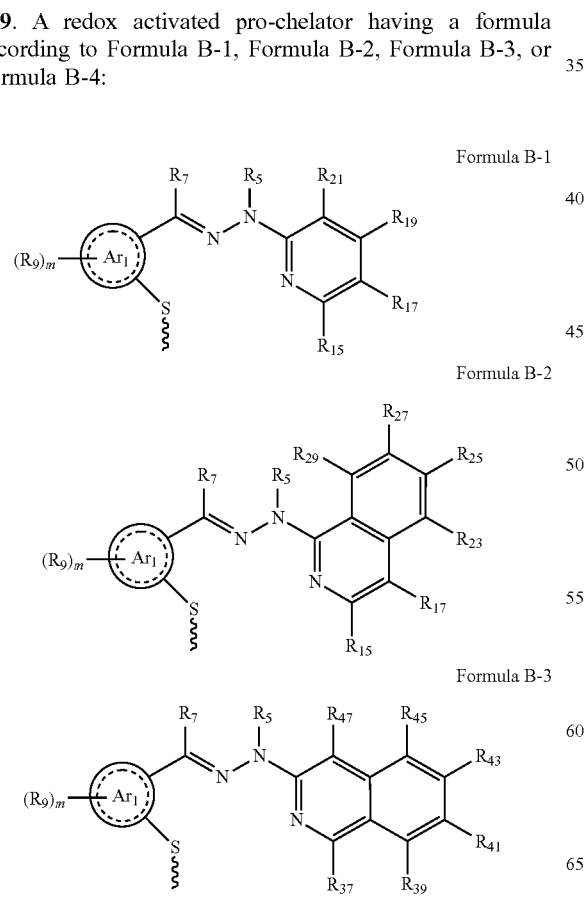

Formula B-1

Formula B-2

Formula B-3

Formula B-4

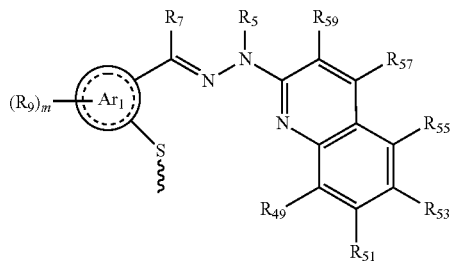

wherein $R_5$, $R_7$, $R_9$, $R_{15}$, $R_{17}$, $R_{19}$, $R_{21}$, $R_{23}$, $R_{25}$, $R_{27}$, $R_{29}$, $R_{37}$, $R_{39}$, $R_{41}$, $R_{43}$, $R_{45}$, $R_{47}$, $R_{49}$, $R_{51}$, $R_{53}$, $R_{55}$, $R_{57}$, and $R_{59}$ are each independently H, Me, Et, Pr, i-Pr, Ph, alkyl, aryl, heteroaryl, substituted alkyl, substituted aryl, substituted heteroaryl, alkoxy, carboxy, hydroxy, amino, phosphate, sulfonate, thiol, nitro, nitrile, halo, an electron withdrawing group, an ion stabilizing group, or an electron stabilizing goup;

wherein m is 0, 1, 2, 3, 4, 5, or 6; and wherein $Ar_1$ is aromatic, substituted aromatic, heteroaromatic, substituted heteroaromatic, phenyl, phenol, furan thiophene, pyrrole, pyridine, imidazole, thiazole, or pyrimidine.

10. The pro-chelator of claim 9, wherein the pro-chelator is according to Formula B-5:

Formula B-5

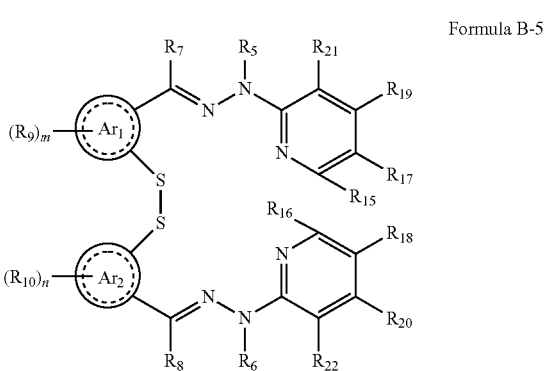

wherein $R_6$, $R_8$, $R_{10}$, $R_{16}$, $R_{18}$, $R_{20}$, and $R_{22}$ are each independently H, Me, Et, Pr, i-Pr, Ph, alkyl, aryl, heteroaryl, substituted alkyl, substituted aryl, substituted heteroaryl, alkoxy, carboxy, hydroxy, amino, phosphate, sulfonate, thiol, nitro, nitrile, halo, an electron withdrawing group, an ion stabilizing group, or an electron stabilizing group;

wherein n is 0, 1, 2, 3 ,4, 5, or 6; and wherein $Ar_2$ is aromatic, substituted aromatic, heteroaromatic, substituted heteroaromatic, phenyl, phenol, furan, thiophene, pyrrole, pyridine, imidazole, thiazole, or pyrimidine.

11. The pro-chelator of claim 9, wherein the pro-chelator is according to Formula B-6:

Formula B-6

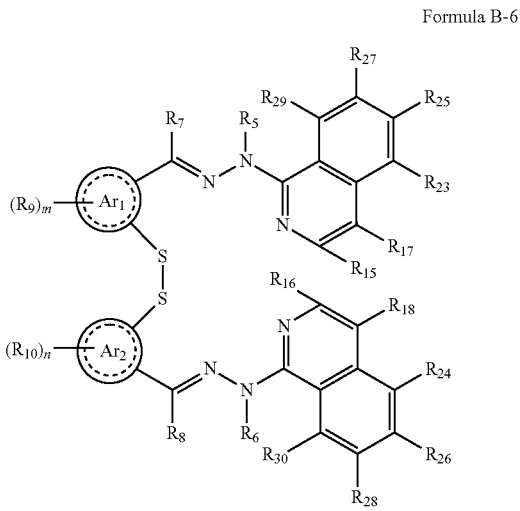

wherein $R_6$, $R_8$, $R_{10}$, $R_{16}$, $R_{18}$, $R_{24}$, $R_{28}$ and $R_{30}$ are each indpendently H, Me, Et, Pr, i-Pr, Ph, alkyl, aryl, heteroaryl, substituted alkyl, substituted aryl, substituted heteroaryl, alkoxy, carboxy, hydroxy, amino, phosphate, sulfonate, thiol, nitro, nitrile, halo, an electron withdrawing group, an ion stabilizing group, or an electron stabilizing group;

wherein n is 0, 1, 2, 3, 4, 5, or 6; and wherein $Ar_2$ is aromatic, substituted aromatic, heteroaromatic, substituted heteroaromatic, phenyl, phenol, furan, thiophene, pyrrole, pyridine, imidazole, thiazole, or pyrimidine.

12. The pro-chelator of claim 9, wherein the pro-chelator is according to Formula B-7:

Formula B-7

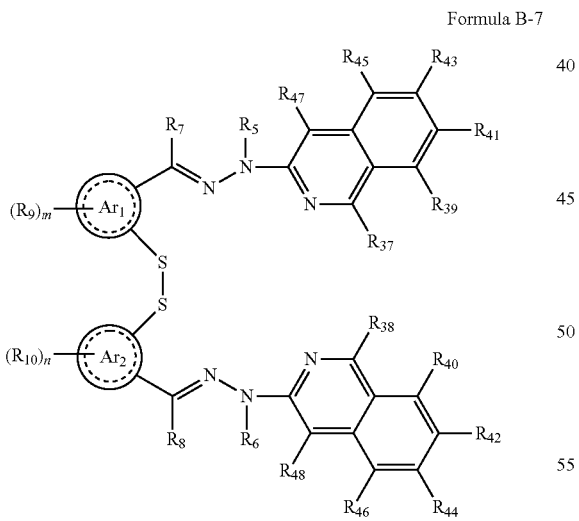

wherein $R_6$, $R_8$, $R_{10}$, $R_{38}$, $R_{40}$, $R_{42}$, $R_{44}$, $R_{46}$ and $R_{48}$ are each independently H, Me, Et, Pr, i-Pr, Ph, alkyl, aryl, heteroaryl, substituted alkyl, substituted aryl, substituted heteroaryl, alkoxy, carboxy, hydroxy, amino, phosphate, sulfonate, thiol, nitro, nitrile, halo, an electron withdrawing group, an ion stabilizing group, or an electron stabilizing group;

wherein n is 0, 1, 2, 3, 4, 5, or 6; and wherein $Ar_2$ is aromatic, substituted aromatic, heteroaromatic, substituted heteroaromatic, phenyl, phenol, furan, thiophene, pyrrole, pyridine, imidazole, thiazole, or pyrimidine.

13. The pro-chelator of claim 9, wherein the pro-chelator is according to Formula B-8:

Formula B-8

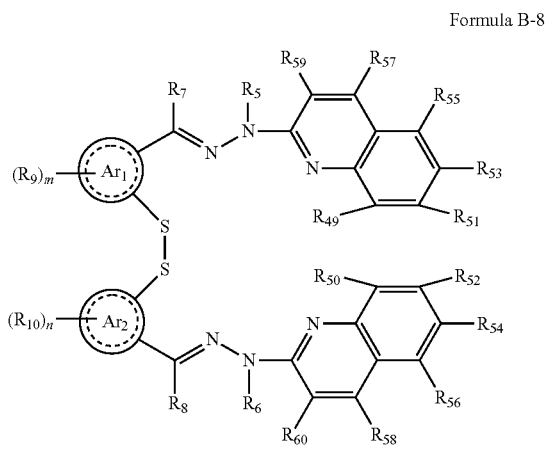

wherein $R_6$, $R_8$, $R_{10}$, $R_{50}$, $R_{52}$, $R_{54}$, $R_{56}$, $R_{58}$ and $R_{60}$ are each independently H, Me, Et, Pr, i-Pr, Ph, alkyl, aryl, heteroaryl, substituted alkyl, substituted aryl, substituted heteroaryl, alkoxy, carboxy, hydroxy, amino, phosphate, sulfonate, thiol, nitro, nitrile, halo, an electron withdrawing group, an ion stabilizing group, or an electron stabilizing group;

wherein n is 0, 1, 2, 3, 4, 5, or 6; and wherein $Ar_2$ is aromatic, substituted aromatic, heteroaromatic, substituted heteroaromatic, phenyl, phenol, furan, thiophene, pyrroe, pyridine, imidazole, thiazole, or pyrimidine.

* * * * *